US011278712B2

(12) United States Patent
Greatrex et al.

(10) Patent No.: US 11,278,712 B2
(45) Date of Patent: Mar. 22, 2022

(54) HEART PUMP WITH IMPELLER ROTATIONAL SPEED CONTROL

(71) Applicant: BiVACOR Inc., Houston, TX (US)

(72) Inventors: Nicholas Greatrex, Cornubia (AU); Daniel Timms, Long Beach, CA (US); Matthias Kleinheyer, Aspley (AU)

(73) Assignee: BiVACOR Inc., Houston, TX (US)

( * ) Notice: Subject to any disclaimer, the term of this patent is extended or adjusted under 35 U.S.C. 154(b) by 111 days.

(21) Appl. No.: 16/028,949

(22) Filed: Jul. 6, 2018

(65) Prior Publication Data

US 2018/0311422 A1 Nov. 1, 2018

Related U.S. Application Data

(63) Continuation of application No. PCT/US2017/012506, filed on Jan. 6, 2017.
(Continued)

(51) Int. Cl.
*A61M 60/50* (2021.01)
*A61M 60/82* (2021.01)
(Continued)

(52) U.S. Cl.
CPC .......... *A61M 60/82* (2021.01); *A61M 60/122* (2021.01); *A61M 60/148* (2021.01);
(Continued)

(58) Field of Classification Search
CPC .. A61M 1/1015; A61M 1/1036; A61M 1/122; A61M 1/101; A61M 1/1086;
(Continued)

(56) References Cited

U.S. PATENT DOCUMENTS 2,700,343 A   1/1955  Pezzillo, Jr.
4,135,253 A   1/1979  Reich et al.
(Continued)

FOREIGN PATENT DOCUMENTS

CA      2638958 C    11/2011
CN   101873870 A    10/2010
(Continued)

OTHER PUBLICATIONS

Sonune, et al,, "Performance Investigation of Centrifugal Pump By Varying Blade Angles of the Impeller-A" IJCET INPRESSO Special Issue—7 (Mar. 2017), pp. 399-401.
(Continued)

*Primary Examiner* — Eric D. Bertram
(74) *Attorney, Agent, or Firm* — Goodwin Procter LLP

(57) ABSTRACT

A heart pump including a housing forming a cavity including at least one inlet and at least one outlet, an impeller provided within the cavity, the impeller including vanes for urging fluid from the inlet to the outlet upon rotation of the impeller, a drive that rotates the impeller within the cavity, a magnetic bearing including at least one bearing coil that controls an axial position of the impeller within the cavity and a controller. The controller includes an electronic processing device that monitors changes in a bearing indicator in response to a perturbation in blood flow, the bearing indicator being at least partially indicative of operation of the magnetic bearing and controls the drive to thereby selectively change a rotational speed of the impeller at least partially in accordance with changes in the bearing indicator.

19 Claims, 23 Drawing Sheets

Related U.S. Application Data

(60) Provisional application No. 62/275,754, filed on Jan. 6, 2016, provisional application No. 62/275,723, filed on Jan. 6, 2016, provisional application No. 62/275,744, filed on Jan. 6, 2016.

(51) Int. Cl.

| | | |
|---|---|---|
| *A61M 60/122* | (2021.01) | |
| *A61M 60/148* | (2021.01) | |
| *A61M 60/205* | (2021.01) | |
| *A61M 60/419* | (2021.01) | |
| *A61M 60/422* | (2021.01) | |
| *F04D 1/00* | (2006.01) | |
| *F04D 29/048* | (2006.01) | |
| *F04D 29/24* | (2006.01) | |
| *F04D 29/42* | (2006.01) | |

(52) U.S. Cl.
CPC ........ *A61M 60/205* (2021.01); *A61M 60/419* (2021.01); *A61M 60/422* (2021.01); *A61M 60/50* (2021.01); *F04D 1/00* (2013.01); *F04D 29/048* (2013.01); *F04D 29/242* (2013.01); *F04D 29/4293* (2013.01); *A61M 2205/3334* (2013.01); *A61M 2205/3365* (2013.01); *A61M 2206/14* (2013.01); *A61M 2206/20* (2013.01); *A61M 2230/04* (2013.01); *A61M 2230/30* (2013.01)

(58) Field of Classification Search
CPC .. A61M 2205/3334; A61M 2205/3365; A61M 2230/04; A61M 60/515–569
See application file for complete search history.

(56) References Cited

U.S. PATENT DOCUMENTS

| | | |
|---|---|---|
| 4,589,822 A | 5/1986 | Clausen et al. |
| 5,041,934 A | 8/1991 | Stefansky |
| 5,195,877 A | 3/1993 | Kletschka |
| 5,601,418 A | 2/1997 | Ohara et al. |
| 5,613,935 A | 3/1997 | Jarvik |
| 5,725,357 A | 3/1998 | Nakazeki et al. |
| 5,840,070 A | 11/1998 | Wampler |
| 5,851,174 A | 12/1998 | Jarvik et al. |
| 5,890,883 A | 4/1999 | Golding et al. |
| 5,928,131 A | 7/1999 | Prem |
| 5,971,023 A | 10/1999 | Clague et al. |
| 6,017,903 A | 1/2000 | Slusher et al. |
| 6,048,363 A | 4/2000 | Nagyszalanczy et al. |
| 6,074,180 A * | 6/2000 | Khanwilkar .......... F04D 29/041 417/356 |
| 6,179,773 B1 | 1/2001 | Prem et al. |
| 6,220,832 B1 | 4/2001 | Schob |
| 6,227,797 B1 | 5/2001 | Watterson et al. |
| 6,234,772 B1 | 5/2001 | Wampler et al. |
| 6,264,635 B1 | 7/2001 | Wampler et al. |
| 6,293,901 B1 | 9/2001 | Prem |
| 6,312,443 B1 | 11/2001 | Stone |
| 6,351,048 B1 | 2/2002 | Schob et al. |
| 6,394,769 B1 | 5/2002 | Bearnson et al. |
| 6,422,838 B1 | 7/2002 | Sloteman |
| 6,527,698 B1 | 3/2003 | Kung et al. |
| 6,547,530 B2 | 4/2003 | Ozaki et al. |
| 6,575,717 B2 | 6/2003 | Ozaki et al. |
| 6,589,030 B2 | 7/2003 | Ozaki |
| 6,626,644 B2 | 9/2003 | Ozaki |
| 6,638,011 B2 | 10/2003 | Woodard et al. |
| 6,664,714 B2 | 12/2003 | Magnussen et al. |
| 6,688,861 B2 | 2/2004 | Wampler |
| 6,690,101 B2 | 2/2004 | Magnussen et al. |
| 6,717,311 B2 | 4/2004 | Locke |
| 6,790,171 B1 | 9/2004 | Grundeman et al. |
| 6,866,625 B1 | 3/2005 | Ayre et al. |
| 6,870,304 B2 | 3/2005 | Magnussen et al. |
| 7,229,474 B2 | 6/2007 | Hoffmann et al. |
| 7,274,131 B2 | 9/2007 | Li et al. |
| 7,435,059 B2 | 10/2008 | Smith et al. |
| 7,439,652 B2 | 10/2008 | Ganor et al. |
| 7,462,019 B1 | 12/2008 | Allarie et al. |
| 7,476,077 B2 | 1/2009 | Woodard et al. |
| 7,645,225 B2 | 1/2010 | Medvedev et al. |
| 7,704,054 B2 | 4/2010 | Horvath et al. |
| 7,914,436 B1 | 3/2011 | Kung |
| 7,931,581 B2 | 4/2011 | Cohn |
| 8,110,967 B2 | 2/2012 | Ting et al. |
| 8,210,829 B2 | 7/2012 | Horvath et al. |
| 8,226,373 B2 | 7/2012 | Yaegashi |
| 8,506,471 B2 | 8/2013 | Bourque |
| 8,551,163 B2 | 10/2013 | Aber et al. |
| 8,613,696 B2 | 12/2013 | Medvedev et al. |
| 8,636,638 B2 * | 1/2014 | Timms .................. F04D 29/048 600/16 |
| 8,747,293 B2 | 6/2014 | Arndt et al. |
| 8,834,345 B2 | 9/2014 | Yanai et al. |
| 8,961,388 B2 | 2/2015 | Bourque |
| 9,011,312 B2 | 4/2015 | Bourque |
| 9,095,428 B2 | 8/2015 | Kabir et al. |
| 9,371,826 B2 | 6/2016 | Yanai et al. |
| 9,427,508 B2 | 8/2016 | Reyes et al. |
| 9,433,717 B2 | 9/2016 | Bourque |
| 9,492,601 B2 | 11/2016 | Casas et al. |
| 9,511,179 B2 | 12/2016 | Casas et al. |
| 9,512,852 B2 | 12/2016 | Wampler et al. |
| 9,709,061 B2 | 7/2017 | Yanai et al. |
| 9,801,988 B2 | 10/2017 | Bourque |
| 9,901,666 B2 | 2/2018 | Cotter |
| 10,077,777 B2 | 9/2018 | Horvath et al. |
| 10,086,122 B2 | 10/2018 | Bourque |
| 2002/0094281 A1 | 7/2002 | Khanwilkar et al. |
| 2002/0109621 A1 | 8/2002 | Khair et al. |
| 2003/0023131 A1 | 1/2003 | Antaki |
| 2003/0176760 A1 * | 9/2003 | El Oakley ........... A61M 60/135 600/16 |
| 2004/0267344 A1 | 12/2004 | Stett et al. |
| 2005/0214131 A1 | 9/2005 | Miles et al. |
| 2007/0249888 A1 | 10/2007 | Wu et al. |
| 2007/0253842 A1 | 11/2007 | Horvath et al. |
| 2010/0168848 A1 | 7/2010 | Horvath et al. |
| 2011/0118537 A1 | 5/2011 | Wampler |
| 2011/0118619 A1 | 5/2011 | Burton et al. |
| 2011/0148253 A1 | 6/2011 | Friend et al. |
| 2012/0095280 A1 * | 4/2012 | Timms .................. F04D 29/048 600/16 |
| 2012/0245680 A1 | 9/2012 | Masuzawa et al. |
| 2012/0253103 A1 | 10/2012 | Robert |
| 2012/0289897 A1 | 11/2012 | Friend et al. |
| 2014/0100413 A1 | 4/2014 | Casas et al. |
| 2017/0340788 A1 | 11/2017 | Korakianitis et al. |
| 2018/0185567 A1 | 7/2018 | Madhani et al. |
| 2019/0001037 A1 * | 1/2019 | Bonde .................. A61M 60/40 |

FOREIGN PATENT DOCUMENTS

| | | |
|---|---|---|
| CN | 102458498 B | 6/2015 |
| CN | 102711862 B | 12/2015 |
| EP | 1065383 A1 | 1/2001 |
| EP | 1188453 A1 | 3/2002 |
| EP | 1273096 B1 | 11/2005 |
| EP | 1630897 A1 | 3/2006 |
| EP | 1674119 A1 | 6/2006 |
| EP | 1495773 A3 | 11/2006 |
| EP | 1721346 B1 | 10/2007 |
| EP | 2538086 A4 | 4/2015 |
| JP | 7255834 | 10/1995 |
| JP | 2001061957 A | 3/2001 |
| JP | 2001-224568 A | 8/2001 |
| JP | 2003-230547 A | 8/2003 |
| JP | 2004-61251 A | 2/2004 |
| JP | 2005-282675 A | 10/2005 |
| JP | 3930834 B2 | 6/2007 |
| JP | 2009-011767 A | 1/2009 |
| WO | WO-00/32256 A1 | 6/2000 |

(56) References Cited

FOREIGN PATENT DOCUMENTS

| WO | WO-00/32257 A1 | 6/2000 |
|---|---|---|
| WO | WO-2002-053028 A8 | 12/2002 |
| WO | WO-2004-032738 A1 | 4/2004 |
| WO | WO-2004-043252 A1 | 5/2004 |
| WO | WO-2004-047636 A1 | 6/2004 |
| WO | WO-2004098677 A1 | 11/2004 |
| WO | WO-2004-098389 A3 | 3/2005 |
| WO | WO-2006053384 A1 | 5/2006 |
| WO | WO-2007/056493 A1 | 5/2007 |
| WO | WO-2007/084339 A3 | 1/2008 |
| WO | WO-2009/058726 A1 | 5/2009 |
| WO | WO-2010/118475 A1 | 10/2010 |
| WO | WO-2010/118476 A1 | 10/2010 |
| WO | WO-2011/026187 A1 | 3/2011 |
| WO | WO-2011/054545 A1 | 5/2011 |
| WO | WO-2013/033783 A1 | 3/2013 |
| WO | WO-2017/120453 A1 | 7/2017 |
| WO | WO-2017/120451 A3 | 8/2017 |
| WO | WO-2017/120449 A3 | 11/2017 |

OTHER PUBLICATIONS

Gulich, Gentrifugal pumps 2nd Ed (2010), pp. 352-357.
Amano, et al., An ultrasonic actuator with multi-degree of freedom using bending and longitudinal vibrations of a single stator; IEEE Ultrason. Symp. Proc.; pp. 667-670; 1998.
Gaddum, Nicholas Richard, "Passive Control of a Bi-Ventricular Assist Device: An experimental and Numerical Investigation", (Thesis), Queensland University of Technology 2008, Ch. 3, sections 3.4.3.1, 3.4.3.4, 3.6 to 3.7 & Figs. 3-12 to 3-14, 3-16, 3-18, 3-23, 3-25 to 3-27, 3-35 to 3-36; Ch. 8, section 8.2.1.
Gouda et al.; A miniaturization of the multi-degree-of-freedom ultrasonic actuator using a small cylinder fixed on a substrate; Ultrasonics; 44 supp. 1; pp. e617-e620; Dec. 22, 2006.
Greatrex N. et al. 'Axial magnetic bearing . . . ', 2010, IEEE Transactions in Biomedical Eng, vol. 57(3), pp. 714-721.
Kanda et al. A micro ultrasonic motor using a micro-machined cylindrical bulk PZT transducer; Sensors and Actuators; 127; pp. 131-138; Dec. 19, 2009.
Kawano et al.; Application of a multi-DOF ultrasonic servomotor in an auditory tele-existence robot; IEEE Trans. Robotics; 21 (5); pp. 790-800; Oct. 2005.
Khoo et al.; Triple degree-of-freedom piezoelectric micromotor via flexural-axial coupled vibration; IEEE Transactions on ultrasonics, Ferroelectrics, and Frequency Control; 56(8); pp. 1716-1724; Aug. 2009.
Maslen E. et cl. 'Feedback Control Applications in Artificial Hearts . . . ' 1998 IEEE Control Systems Mag, vol. 18(6), pp. 26-34.
Masuzawa T. et al., 'Magnetically Suspended Centrifugal . . . ' 2002, ASAIO Journal, pp. 437-442.
Masuzawa, T., H. Onuma, and Y. Okada, "Zero Power Control for Magnetically Suspended Artificial Heart." Jido Seigyo Rengo Koenkai Koen Ronbunshu, 2004. 47: p. 322.
Masuzawa, Toru et al., "An Ultradurable and Compact Rotary Blood Pump with a Magnetically Suspended Impeller in the Radial Direction", Artificial Organs, vol. 25, Issue 5, 2001, pp. 395-399, Abstract; Suspension system (pp. 396-397); Discussion (p. 398); Figs. 1-6.
Masuzawa, Toru et al., "Magnetically Suspended Centrifugal Blood Pump with an Axially Levitated Motor", Artificial Organs, vol. 27, Issue 7, 2003, pp. 631-638 Abstract; axially levitated motor (pp. 632-633); Motor design and experimental set-up (pp. 633-634); levitation performance (pp. 634-635); Discussion (pp. 636-638); Figs. 1,3-5, 8 and 13.
Masuzawa, Toru et al., "Magnetically Suspended Rotary Blood Pump with Radial Type Combined Motor-Bearing", Artificial Organs, vol. 24, Issue 6, 2000, pp. 468-474, Abstract; Suspension control (pp. 468-469); Prototype of the magnetically suspended centrifugal pump (pp. 469-470); Discussion (p. 471); Figs. 1-6.
Morita, et al.; A cylindrical micro ultrasonic motor using PZT thin film deposited by single process hydrothermal method (Ø2.4 mm, L=10 mm stator transducer); IEEE Trans. Ferroelectr. Freq. Contrl; 45(5); pp. 1178-1187; Sep. 1998.
Niwano, et al.; An active dummy head driven by a multi-degree-of-freedom ultrasonic actuator; WCU Conf. Proc. 1597; 2003.
Park, et al.; Study on multi-DOF ultrasonic actuator for laparoscopic instrument; JSME int. J.; 47(2); pp. 574-581; 2004.
Rogers; A diameter 300 µm bragg reflector for acoustic isolation of resonant micro-actuators; J. Micromech. Microeng. 21 (4 ); pp. 1-4; Apr. 2011.
Rogers; Piezoelectric ultrasonic micro-motor system for minimally invasive surgery—the intellimotor; AIP Conf. Proc. 1433 pp. 705-708; 2012.
Rogers; Three degree-of-freedom piezoelectric ultrasonic micromotor with a major diameter of 350 µm; J. Micromech. Microeng.;20(12); pp. 1-5; Dec. 2010.
Satoshi Ueno et al., "Characteristics of axial force and rotating torque and their control of permanent magnet type axial gap self-bearing motor", Electrical Engineering in Japan, vol. 132, Issue 1, 2000, pp. 81-91 (whole document).
Sin, D.C. et al., "Blood flow in a double output centrifugal artificial heart pump as a biventricular assist device", ANZIAM J. 48 (CTAC2006), Feb. 27, 2008, pp. C949-C962, Materials and Method section (pp. C952-C955); Figures 2-4.
Takemura et al.; Characterstics of an ultrasonic motor capable of generating a multi-degrees of freedom motion; Proc. IEEE int. Conf, on Robotics and Automation; vol. 4; pp. 3660-3665; Apr. 2000.
Takemura et al.; Control of multi-dof ultrasonic actuator for dexterous surgical instrument; Journal of Sound and Vibration; 311; pp. 652-666; Nov. 26, 2007.
Timms, D.L., "Design, Development and Evaluation of Centrifugal Type Ventricular Assist Devices", (Thesis), Queensland University of Technology, 2005 Ch. 4, sections 4.4.4-3 BiLVAD and 4.4.4 Bi-VAD & Figure 4-20 to 4-21; Ch. 5—VAD Experimental Evaluation; Ch. 6, VAD Summary & Figures 6-1 to 6-8.
Wajchman et al.; An ultrasonic piezoelectric motor utilizing axial-torsional coupling in a pretwisted non-circular cross-sectioned primatic beam; IEEE Transactions of Ultrasonics, Ferroelectrics, and Frequency Control; 55(4); pp. 832-840; Apr. 2008.
Watson Peizoelectric ultrasonic micro/milli-scale actuators; Sensors Actuators; 152; pp. 219-233; Apr. 2, 2009.

* cited by examiner

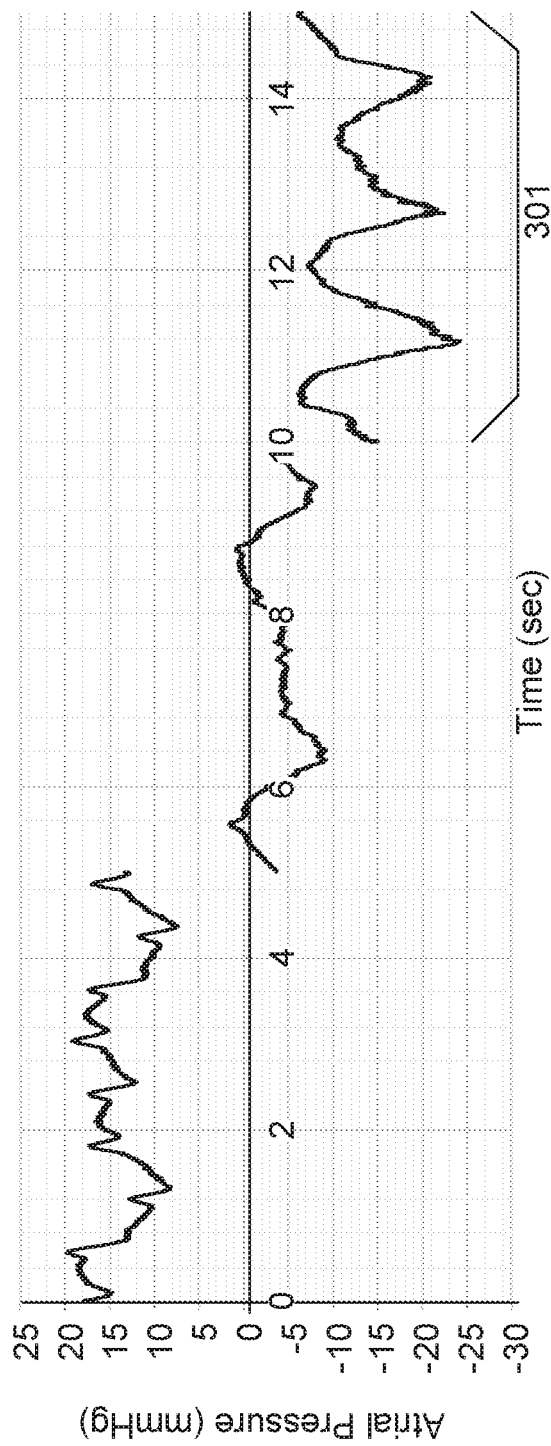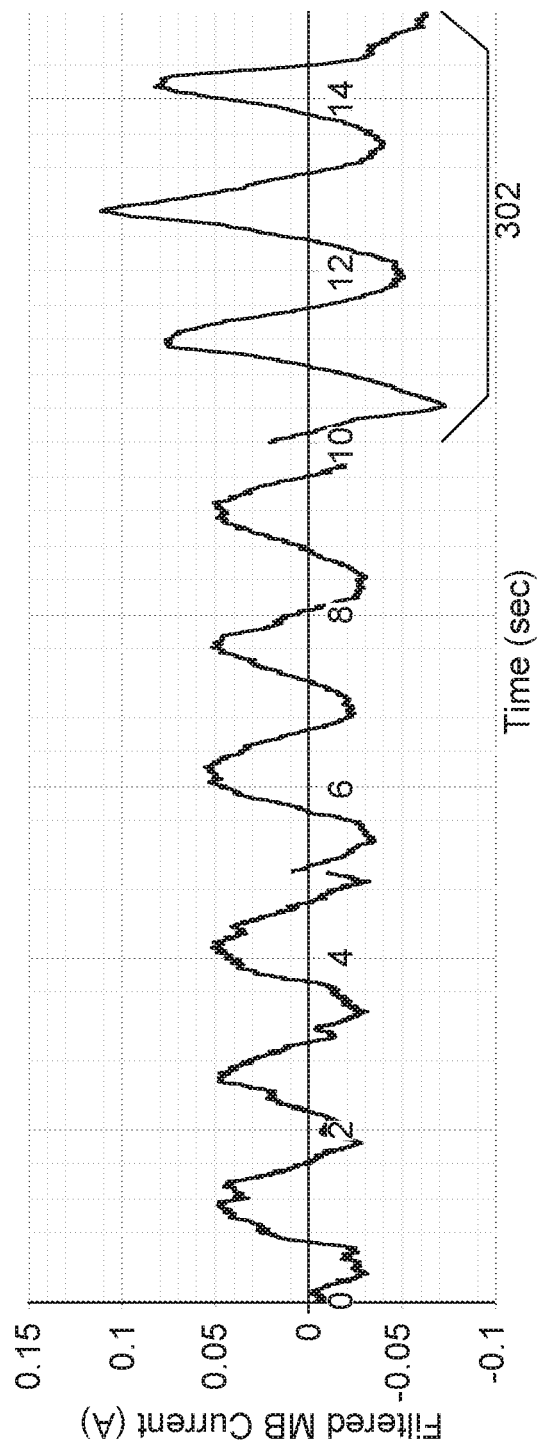

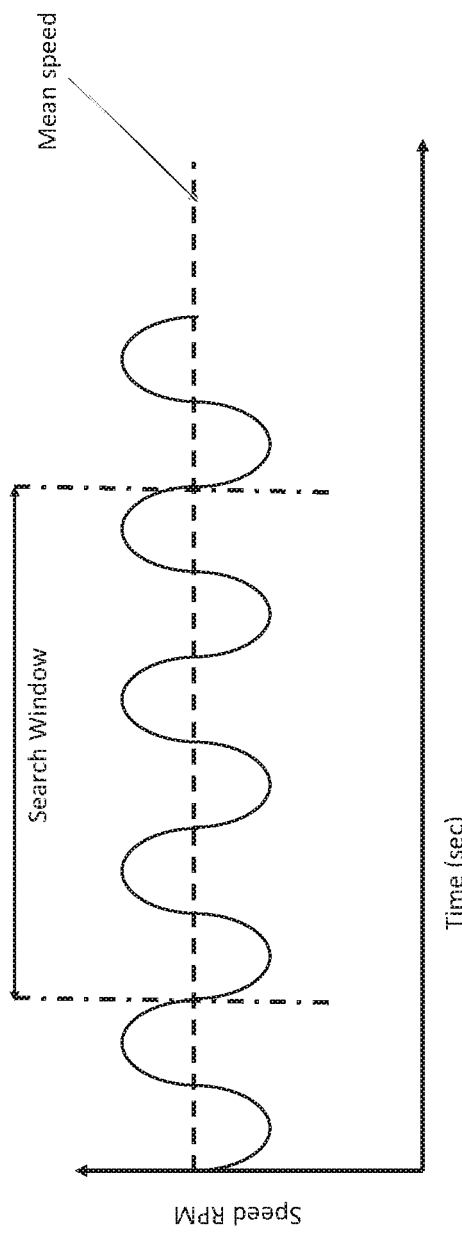
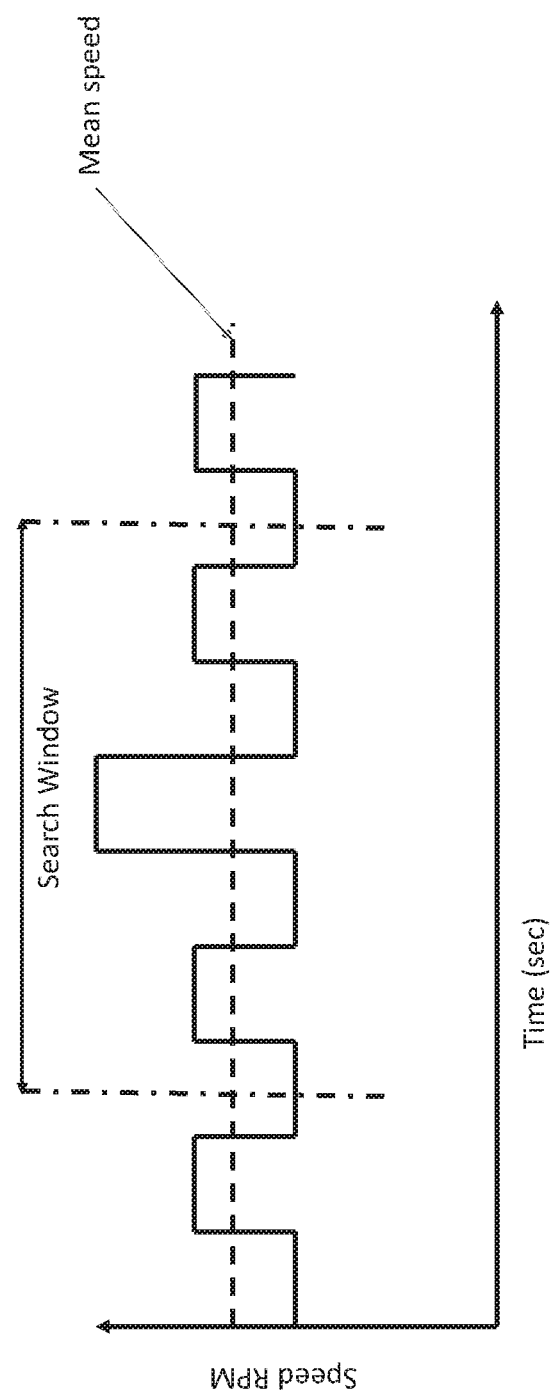

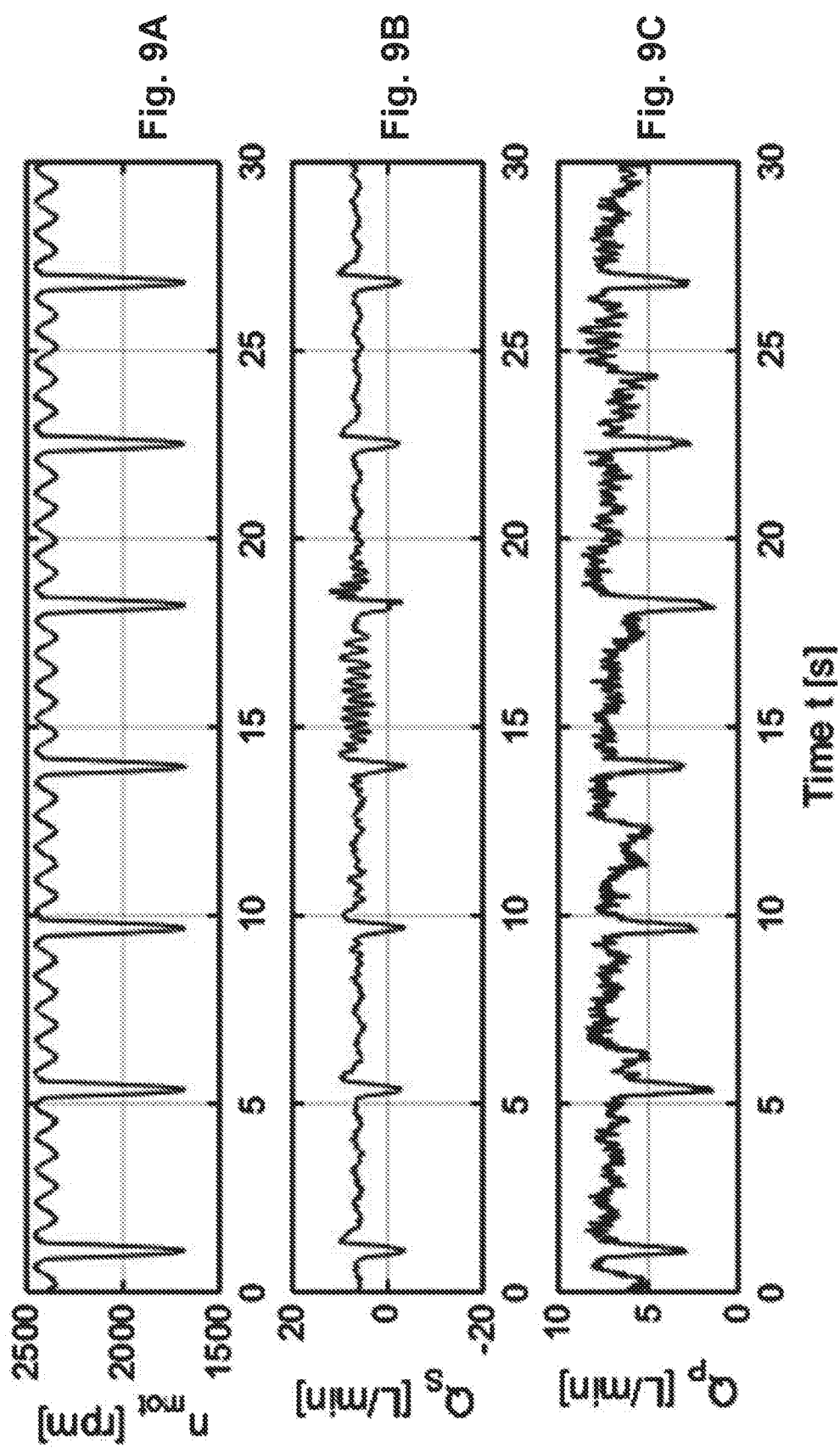

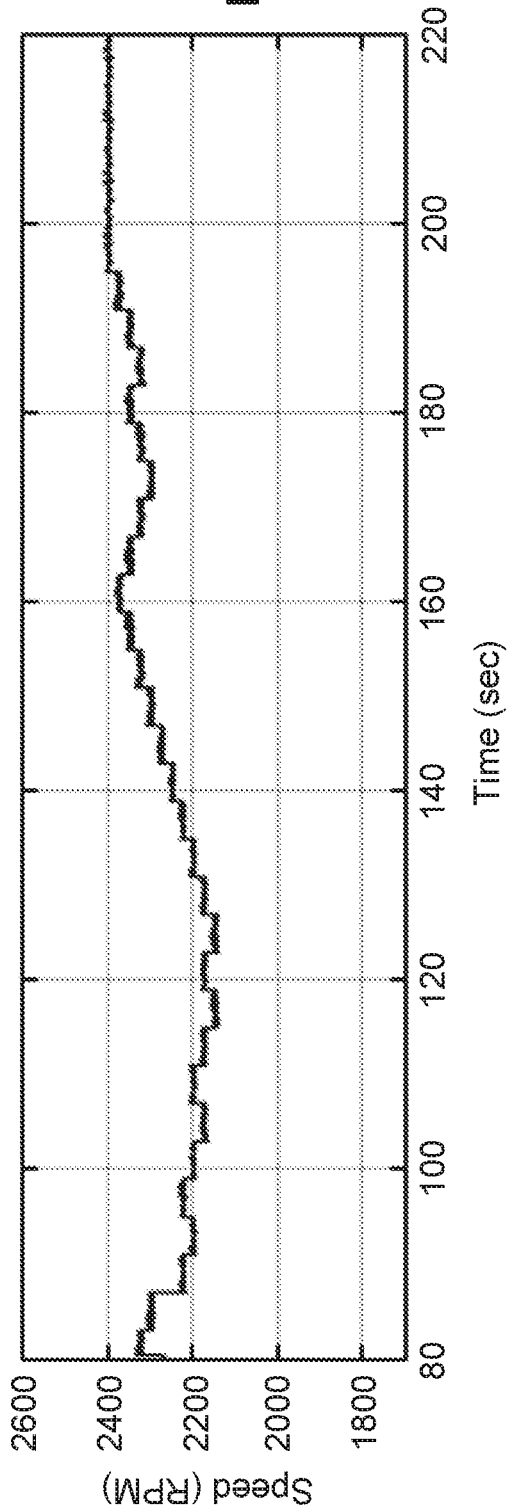

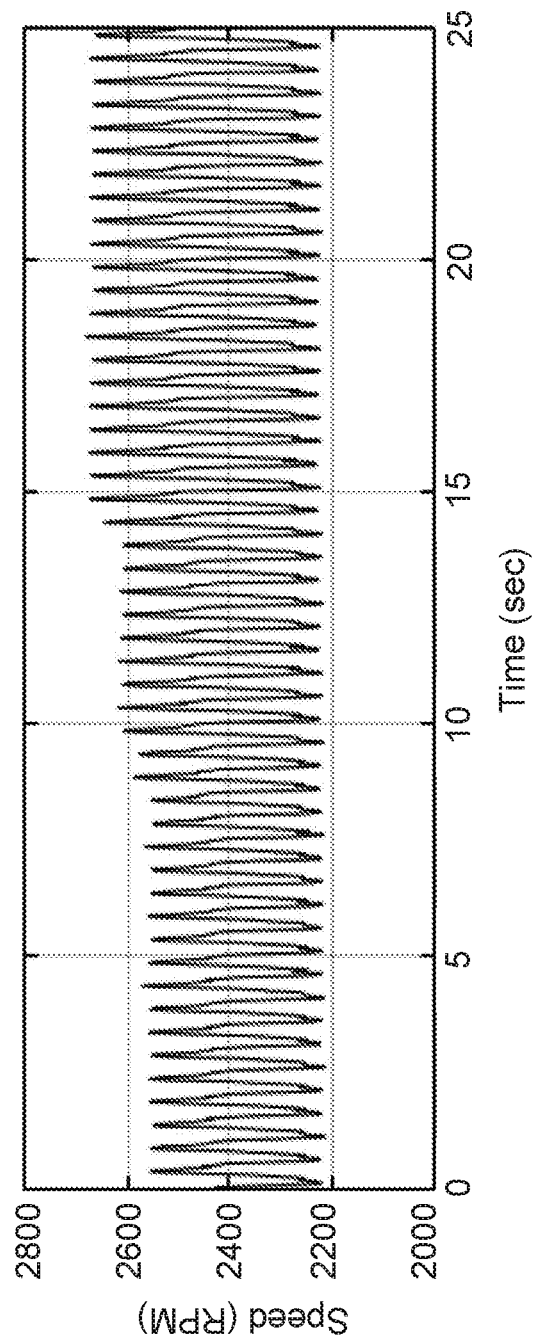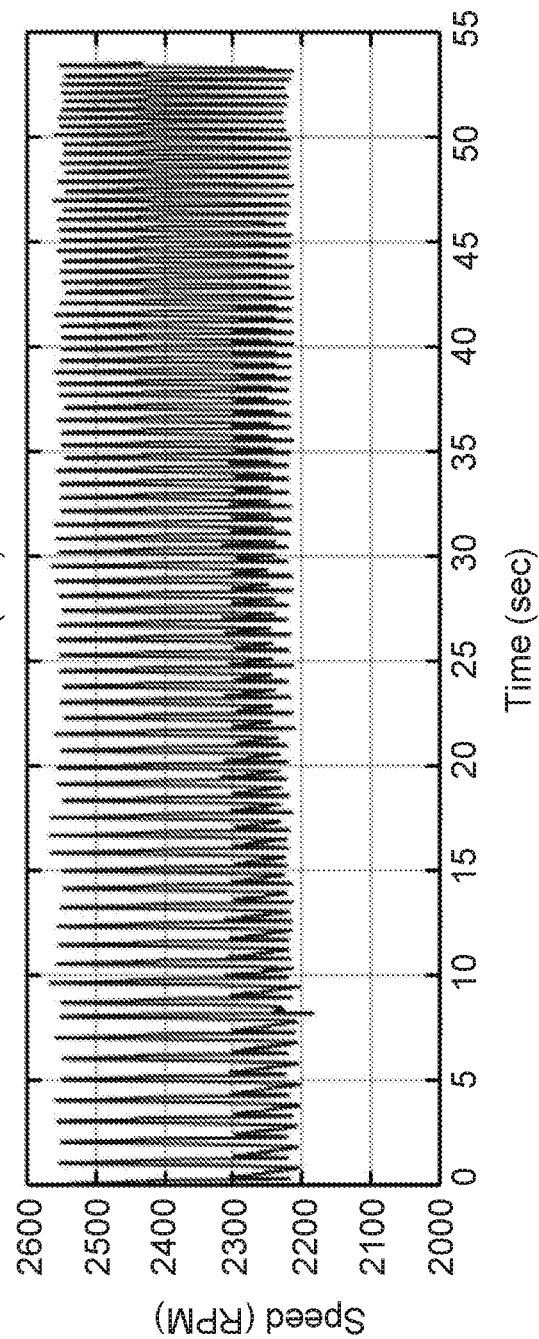

HEART PUMP WITH IMPELLER ROTATIONAL SPEED CONTROL

CROSS-REFERENCE TO RELATED APPLICATIONS

This application claims the benefit of priority under 35 U.S.C. § 120 to International Patent Application No. PCT/US2017/012506 entitled "Heart Pump With Impeller Rotational Speed Control," filed on Jan. 6, 2017 which claims priority under 35 U.S.C. § 119 to U.S. Provisional Patent Application No. 62/275,754 entitled "Heart Pump," filed on Jan. 6, 2016; U.S. Provisional Patent Application No. 62/275,723 entitled "Heart Pump Impeller Rotational Speed Control," filed on Jan. 6, 2016; and U.S. Provisional Patent Application No. 62/275,744 entitled "Heart Pump With Impeller Axial Position Control," filed on Jan. 6, 2016, the contents of all of which are incorporated herein by reference in their entireties.

BACKGROUND OF THE INVENTION

The present invention relates to a heart pump and in particular to a method of controlling a rotational speed of an impeller in a heart pump.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

The use of rotary impeller based mechanical pumps to treat heart failure is increasing as the general population ages and the number of donor organs for heart transplantation remains limited. Devices can be used to bridge a patient to heart trans-plant, to recovery, or indeed as a destination alternative.

WO2004098677 and WO2006053384A1 each describe a double sided impeller that rotates at a common speed, with each side of the impeller respectively configured for left and right heart assistance. This effectively introduces an inherent problem regarding the ability to independently control and thus balance the outflow from the left and right sides of the device, i.e. an increase in impeller rotational speed with produce a corresponding increase in outflow from both cavities.

WO2006053384A1 addressed this issue by introducing the ability to axially displace the rotating impeller within the cavity so as to simultaneously alter the relative efficiencies of each side of the device. However, when the control method used to achieve this axial displacement is active, such pumps require the use of feedback signals from pressure sensors and the like to actively control and maintain a desired set axial location. This method of control would inherently consume excessive amounts of electrical power and introduce issues relating to the long term reliability of blood contacting sensors.

U.S. Pat. No. 8,636,638 describes a controller for a heart pump that determines movement of an impeller within a cavity in a first axial direction, the cavity including at least one inlet and at least one outlet, and the impeller including vanes for urging fluid from the inlet to the outlet, causing a magnetic bearing to move the impeller in a second axial direction opposite the first axial direction, the magnetic bearing including at least one coil for controlling an axial position of the impeller within the cavity, determining an indicator indicative of the power used by the magnetic bearing and causing the magnetic bearing to control the axial position of the impeller in accordance with the indicator to thereby control a fluid flow between the inlet and the outlet.

U.S. Pat. No. 7,435,059 describes a system for pumping blood to assist or assume the cardiac function of a patient is characterized by a blood pump that exhibits a steep pump curve such that only small changes in pump flow occur for large changes in differential pressure across the pump. The pump therefore exhibits flow-limiting characteristics to protect the physiological system against harmful flow rates. Pump flow may also be limited by controlling the current provided to a driver from a power supply or by suitable restrictions within or external to the pump housing.

It is desirable to be able to control the rotational speed of impellers, in order to optimise flow for the particular physiological conditions of a subject. However, detecting and responding to physiological parameters can be difficult, requiring sensors to be implemented within the subject, and ensuring that the pump is controlled appropriately.

SUMMARY OF THE PRESENT INVENTION

In one broad form, one aspect of the invention seeks to provide a heart pump including: a housing forming a cavity including at least one inlet and at least one outlet; an impeller provided within the cavity, the impeller including vanes for urging fluid from the inlet to the outlet upon rotation of the impeller; a drive that rotates the impeller within the cavity; a magnetic bearing including at least one bearing coil that controls an axial position of the impeller within the cavity; and, a controller including an electronic processing device that: monitors changes in a bearing indicator in response to a perturbation in blood flow, the bearing indicator being at least partially indicative of operation of the magnetic bearing; and, controls the drive to thereby selectively change a rotational speed of the impeller at least partially in accordance with changes in the bearing indicator.

In one embodiment the bearing indicator is indicative of at least one of: a tilt of the impeller; an electrical current used by the magnetic bearing; and, an axial position of the impeller within the cavity.

In one embodiment the bearing indicator is indicative of at least one of: a change in tilt of the impeller; a rate of change in tilt of the impeller; a change in electrical current used by the magnetic bearing; a rate of change in electrical current used by the magnetic bearing; a change in axial position of the impeller within the cavity; and, a rate of change in axial position of the impeller within the cavity.

In one embodiment the controller: compares the change in bearing indicator to a bearing threshold; and, controls the rotational speed in response to results of the comparison.

In one embodiment the controller: selectively decreases the rotational speed of the impeller in response to the change in bearing indicator exceeding the bearing threshold; and, selectively increases the rotational speed of the impeller in response to the change in bearing indicator not exceeding the bearing threshold.

In one embodiment the controller: compares the bearing indicator change to multiple bearing thresholds; and, controls the rotational speed in response to results of the comparison.

In one embodiment the bearing threshold is adjusted based on at least one of: changes in rotational speed of the impeller; and, an impeller position.

In one embodiment the controller: determines a number of successive rotational speed changes; compares the number to a respective threshold; and, adjusts the bearing threshold in response to the results of the comparison.

In one embodiment the controller: monitors the bearing indicator over a set time period; determines a maximum change in bearing indicator during the set time period; and, compares the maximum change to the bearing threshold.

In one embodiment the change in bearing indicator is at least partially indicative of at least one of: a set blood pressure; a suction event; connection conduit collapse; connection conduit deformation; vasculature collapse; and, vasculature deformation.

In one embodiment the controller selects the bearing threshold based on a drive indicator at least partially indicative of operation of the drive.

In one embodiment the controller: determines a drive indicator at least partially indicative of operation of the drive; determines a combined indicator based on a combination of the bearing indicator and the drive indicator; and, controls the drive to thereby selectively change a rotational speed of the impeller at least partially in accordance with the combined indicator.

In one embodiment the controller: compares a change in the combined indicator to a combined indicator threshold; and, controls the rotational speed in response to results of the comparison.

In one embodiment the controller determines the combined indicator by at least one of: multiplying the bearing and motor indicators; dividing the bearing and motor indicators; determining a ratio of the bearing and motor indicators; adding the bearing and motor indicators; subtracting the bearing and motor indicators; determining a weighted sum of the bearing and motor indicators; determining a log sum of the bearing and motor indicators; determining a weighted integral of bearing and motor signals; and, determining a convolution of the bearing and motor indicators.

In one embodiment the drive indicator is indicative of at least one of: a current supplied to the drive; an expected rotational speed of the impeller; an actual rotational speed of the impeller; and, a magnitude of a rotational speed change.

In one embodiment the perturbation is at least one of: a physiological perturbation; and, a pump operation perturbation; and, In one embodiment the perturbation includes at least one of: a heart beat of a subject; aspiration of a subject; a change in pump rotational speed; and, a change in axial position of the impeller.

In one embodiment the controller controls the drive to periodically alter the rotational speed of the impeller and thereby cause the perturbation.

In one embodiment the controller monitors changes in the bearing indicator at least partially in accordance with a frequency of the perturbations.

In one embodiment the controller controls the rotational speed of the impeller so as to maximize the rotational speed of the impeller whilst avoiding a low pressure condition including at least one of: a suction event; connection conduit collapse; connection conduit deformation; vasculature collapse; and, vasculature deformation; and, In one embodiment the controller: uses the change in bearing indicator to determine an onset of a low pressure condition including at least one of: a suction event; connection conduit collapse; connection conduit deformation; vasculature collapse; and, vasculature deformation; and, selectively decreases the rotational speed of the impeller in response to the onset being detected.

In one embodiment the controller records an indication of at least one of: the bearing indicator change; the bearing indicator; and, the rotational speed of the impeller.

In one embodiment the impeller includes first and second sets of vanes provided on a rotor body, the rotor being positioned within the cavity to define: a first cavity portion having a first inlet and a first outlet, the first set of vanes being provided within the first cavity portion so as to define a first pump that provides at least partial left ventricular function; and, a second cavity portion having a second inlet and a second outlet, the second set of vanes being provided within the second cavity portion so as to define a second pump that provides at least partial right ventricular function.

In one embodiment the axial position of the impeller determines a separation between each set of vanes and a respective cavity surface, the separation being used to control the fluid flows from the inlets to the outlets.

In one embodiment the first and second pumps have respective pump performance curve having different gradients so that a change in rotational speed of the pump causes a change in the relative flows of the first and second pumps.

In one embodiment the drive includes: a number of circumferentially spaced permanent magnets mounted in the rotor of the impeller, adjacent magnets having opposing polarities; at least one drive coil that in use generates a magnetic field that cooperates with the magnetic material allowing the impeller to be rotated.

In one embodiment the magnetic bearing includes: first and second annular magnetic bearing members mounted within and proximate a face of the rotor, the first magnetic bearing member being provided radially outwardly of the second magnetic bearing member; a number of circumferentially spaced substantially U-shaped bearing stators mounted in the housing proximate a second end of the cavity, each U-shaped bearing stator having first and second bearing stator legs substantially radially aligned with the first and second magnetic bearing members respectively; and, at least one bearing coil on each bearing stator that generates a magnetic field that cooperates with the magnetic bearing members to thereby at least one of: control an axial position of the impeller; and, at least partially restrain radial movement of the impeller.

In one embodiment the drive is positioned at a first end of the cavity and the magnetic bearing is positioned at a second end of the cavity.

In one embodiment the heart pump is at least one of: a ventricular assist device; and, a total artificial heart.

In one embodiment the controller controls the drive to selectively change a rotational speed of the impeller and thereby vary a blood flow rate through the heart pump to thereby induce at least one pulse.

In one embodiment the controller is adapted to control an overall flow rate through the pump by controlling at least one of: a pulse magnitude defined by a difference between an upper and lower rotational speed; and, a pulse frequency.

In one embodiment the change in rotational speed is performed so as to induce a pulsatile flow including a series of pulses, and wherein for each pulse the controller: creates a spike in rotational speed; creates a first peak in rotational speed, the first peak having a magnitude smaller than the spike; and, creates a second peak in rotational speed, the second peak having a magnitude smaller than the first peak.

In one embodiment the change in rotational speed is performed so as to periodically reduce the rotational speed from a baseline speed at least one of: to below a threshold value to create a washout pulse; to induce a physiological pulse.

In one embodiment the controller: monitors operating parameters of the heart pump to detect a trigger; and, at least one of: in response to detection of a trigger at least one of: controls the drive to rotate the impeller at a set rotational speed; and, generates an alert indicative of the trigger; and, in response to no detection of a trigger, controls the drive to rotate the impeller at a target rotational speed determined at least partially in accordance with a cardiac demand.

In one broad form, one aspect of the invention seeks to provide a controller for a heart pump, the controller including an electronic processing device that: monitors changes in a bearing indicator in response to a perturbation in blood flow, the bearing indicator being at least partially indicative of operation of a magnetic bearing including at least one bearing coil that controls an axial position of an impeller within a cavity; and, controls a drive that rotates the impeller within the cavity to thereby selectively change a rotational speed of the impeller at least partially in accordance with changes in the bearing indicator.

In one broad form, one aspect of the invention seeks to provide a method of controlling a heart pump, the method including: monitoring changes in a bearing indicator in response to a perturbation in blood flow, the bearing indicator being at least partially indicative of operation of a magnetic bearing including at least one bearing coil that controls an axial position of an impeller within a cavity; and, controlling a drive that rotates the impeller within the cavity to thereby selectively change a rotational speed of the impeller at least partially in accordance with the bearing indicator change.

In one broad form, one aspect of the invention seeks to provide a heart pump including: a housing forming a cavity including at least one inlet and at least one outlet; an impeller provided within the cavity, the impeller including vanes for urging fluid from the inlet to the outlet upon rotation of the impeller; a drive that rotates the impeller within the cavity; and, a controller including an electronic processing device that: determines an onset of a low pressure condition; and, controls the rotational speed of the impeller so as to maximize the rotational speed of the impeller whilst avoiding the low pressure condition by selectively decreasing the rotational speed of the impeller in response to the onset being detected.

In one embodiment the controller determines an onset of a low pressure condition in accordance with at least one of: an axial position of the impeller within the cavity; a drive indicator at least partially indicative of operation of the drive; and, a bearing indicator at least partially indicative of operation of a magnetic bearing that controls an axial position of the impeller within the cavity.

In one embodiment the drive indicator is indicative of at least one of: a current supplied to the drive; an expected rotational speed of the impeller; an actual rotational speed of the impeller; and, a magnitude of a rotational speed change.

In one embodiment the bearing indicator is indicative of at least one of: a tilt of the impeller; an electrical current used by the magnetic bearing; and, an axial position of the impeller within the cavity.

In one embodiment the axial position of the impeller is determined using a position sensor.

In one embodiment the controller: determines a drive indicator at least partially indicative of operation of the drive; determines a combined indicator based on a combination of the bearing indicator and the drive indicator; and, controls the drive to thereby selectively change a rotational speed of the impeller at least partially in accordance with the combined indicator.

In one embodiment the controller: compares a change in the combined indicator to a combined indicator threshold; and, controls the rotational speed in response to results of the comparison.

In one embodiment the controller determines the combined indicator by at least one of: multiplying the bearing and motor indicators; dividing the bearing and motor indicators; determining a ratio of the bearing and motor indicators; adding the bearing and motor indicators; subtracting the bearing and motor indicators; determining a weighted sum of the bearing and motor indicators; determining a log sum of the bearing and motor indicators; determining a weighted integral of bearing and motor signals; and, determining a convolution of the bearing and motor indicators.

In one broad form, one aspect of the invention seeks to provide a controller for a heart pump, the controller including an electronic processing device that: determines an onset of a low pressure condition; and, controls a drive that rotates an impeller within a cavity to thereby maximize the rotational speed of the impeller whilst avoiding the low pressure condition by selectively decreasing the rotational speed of the impeller in response to the onset being detected.

In one broad form, one aspect of the invention seeks to provide a method of controlling a heart pump, the method including: determining an onset of a low pressure condition; and, controlling a drive that rotates an impeller within a cavity to thereby maximize the rotational speed of the impeller whilst avoiding the low pressure condition by selectively decreasing the rotational speed of the impeller in response to the onset being detected.

In one broad form, one aspect of the invention seeks to provide a heart pump including: a housing forming a cavity including at least one inlet and at least one outlet; an impeller provided within the cavity, the impeller including vanes for urging fluid from the inlet to the outlet upon rotation of the impeller; a drive that rotates the impeller within the cavity; and, a controller including an electronic processing device that controls the drive to selectively change a rotational speed of the impeller and thereby vary a blood flow rate through the heart pump, the change in rotational speed being performed so as to induce a pulsatile flow including a series of pulses, and wherein for each pulse the controller: creates a spike in rotational speed; creates a first peak in rotational speed, the first peak having a magnitude smaller than the spike; and, creates a second peak in rotational speed, the second peak having a magnitude smaller than the first peak.

In one embodiment, in creating the spike, the controller: rapidly increases the rotational speed to an upper spike value; and, substantially immediately decreases the rotational speed to a lower spike value.

In one embodiment, in creating the peaks, the controller: progressively increases the rotational speed from the lower spike value to a first peak upper value; progressively reduces the rotational speed to a first peak lower value; progressively increases the rotational speed to a second peak upper value, the second peak upper value being lower than the first peak upper value; and, progressively reduces the rotational speed to a second peak lower value.

In one embodiment the second peak lower value is at least one of: approximately equal to the first peak lower value; and, slightly lower than the first peak lower value.

In one embodiment a time period between the first and second peak upper values is less than a time period between the first and second peak lower values.

In one embodiment a magnitude of the spike from second peak lower value to the spike upper value is at least one of: more than 500 rpm; more than 800 rpm; more than 1000 rpm; less than 2500 rpm; less than 2000 rpm; less than 1500 rpm; and, between 1000 rpm and 1500 rpm.

In one embodiment a magnitude of the first peak from the first peak upper to lower values is at least one of: more than 300 rpm; more than 400 rpm; more than 500 rpm; less than 1000 rpm; less than 800 rpm; less than 700 rpm; less than 600 rpm; and, between 500 rpm and 600 rpm.

In one embodiment a magnitude of the second peak from the second peak upper to lower values is at least one of: more than 50 rpm; more than 75 rpm; more than 100 rpm; less than 250 rpm; less than 200 rpm; less than 150 rpm; and, between 100 rpm and 150 rpm.

In one embodiment a magnitude of the pulse is based on an impeller position.

In one embodiment each pulse has a duration that is at least one of: greater than 0.5 seconds; greater than 1.0 seconds; less than 2.0 seconds; less than 1.5 seconds; and, between 1.0 and 1.5 seconds.

In one embodiment at least some pulses are separated by inter-pulse time period.

In one embodiment at least one of: the time taken for the spike is approximately 0.15 to 0.2 times a pulse length; the time taken for the first peak is approximately 0.2 to 0.25 times a pulse length; and, the time taken for the second peak is approximately 0.55 to 0.65 times a pulse length.

In one embodiment the controller is adapted to control an overall flow rate through the pump by controlling at least one of: a pulse magnitude defined by a difference between an upper and lower rotational speed; and, a pulse frequency.

In one broad form, one aspect of the invention seeks to provide a controller for a heart pump, the controller including an electronic processing device that controls a drive to selectively change a rotational speed of an impeller and thereby vary a blood flow rate through the heart pump, the change in rotational speed being performed so as to induce a pulsatile flow including a series of pulses, and wherein for each pulse the controller: creates a spike in rotational speed; creates a first peak in rotational speed, the first peak having a magnitude smaller than the spike; and, creates a second peak in rotational speed, the second peak having a magnitude smaller than the first peak.

In one broad form, one aspect of the invention seeks to provide a method for controlling a heart pump, the method including controlling a drive to selectively change a rotational speed of an impeller and thereby vary a blood flow rate through the heart pump, the change in rotational speed being performed so as to induce a pulsatile flow including a series of pulses, and wherein for each pulse the method includes: creates a spike in rotational speed; creates a first peak in rotational speed, the first peak having a magnitude smaller than the spike; and, creates a second peak in rotational speed, the second peak having a magnitude smaller than the first peak.

In one broad form, one aspect of the invention seeks to provide a heart pump including: a housing forming a cavity including at least one inlet and at least one outlet; an impeller provided within the cavity, the impeller including vanes for urging fluid from the inlet to the outlet upon rotation of the impeller; a drive that rotates the impeller within the cavity; and, a controller including an electronic processing device that controls the drive to selectively change a rotational speed of the impeller, wherein the controller periodically reduces the rotational speed from a baseline speed to create a pulse.

In one embodiment the controller periodically reduces the rotational speed to below a threshold value to create a washout pulse.

In one embodiment the threshold value is at least one of: less than 2000 rpm; less than 1900 rpm; less than 1800 rpm; less than 1700 rpm; less than 1600 rpm; more than 500 rpm less than a set operational speed; more than 600 rpm less than a set operational speed; more than 700 rpm less than a set operational speed; and, more than 800 rpm less than a set operational speed.

In one embodiment the washout pulse has a duration of at least one of: at least 0.2 s; at least 0.5 s; at least 0.7 s; less than 5.0 s; less than 4.0 s; less than 3.0 s; less than 2.0 s; and, less than 1.0 s.

In one embodiment the washout pulse is produced with a frequency that is at least one of: at least once every ten minutes; at least once every five minutes; at least once every minute; at least twice every minute; and, at least five times every minute.

In one embodiment the controller controls the drive to produce different washout pulses, the different washout pulses having at least one of: a different rotational speed threshold; a different duration; and, a different frequency.

In one embodiment the controller reduces the rotational speed to induce a physiological pulse.

In one embodiment the physiological pulse includes first and second troughs in rotational speed, wherein the first trough has a lower speed that the second trough.

In one embodiment the trough with the first trough is shorter than the second trough.

In one broad form, one aspect of the invention seeks to provide a controller for a heart pump, the controller including an electronic processing device that controls a drive to selectively change a rotational speed of an impeller, wherein the controller periodically reduces the rotational speed from a baseline speed to create a pulse.

In one broad form, one aspect of the invention seeks to provide a method of controlling a heart pump, the method including controlling a drive to selectively change a rotational speed of an impeller, wherein the method includes periodically reducing the rotational speed from a baseline speed to create a pulse.

In one broad form, one aspect of the invention seeks to provide a heart pump including: a housing forming a cavity including at least one inlet and at least one outlet; an impeller provided within the cavity, the impeller including vanes for urging fluid from the inlet to the outlet upon rotation of the impeller; a drive that rotates the impeller within the cavity; and, a controller including an electronic processing device that: monitors operating parameters of the heart pump to detect a trigger; and, at least one of: in response to detection of a trigger, controls the drive to rotate the impeller at a set rotational speed; and, in response to no detection of a trigger, controls the drive to rotate the impeller at a target rotational speed determined at least partially in accordance with a cardiac demand.

In one embodiment the heart pump includes a magnetic bearing including at least one bearing coil that controls an axial position of the impeller within the cavity and wherein the operating parameters include a bearing indicator at least partially indicative of operation of the magnetic bearing.

In one embodiment the controller: filters the bearing indicator; compares the filtered bearing indicator to a threshold; and, determines a trigger based on a result of the comparison.

In one embodiment the controller: determines a difference between an expected bearing indicator and a measured bearing indicator; and, compares the difference to a threshold.

In one embodiment the controller filters the bearing indicator using at least one of: a low pass filter having a cut-off of 0.2 Hz; a low pass filter having a cut-off of 25 Hz; and, a low pass filter having a cut-off of 1 Hz. determines a trigger based on a result of the comparison.

In one embodiment the controller: determines a cardiac demand; and, determines the target rotational speed at least partially in accordance with the cardiac demand.

In one embodiment the heart pump includes a magnetic bearing including at least one bearing coil that controls an axial position of the impeller within the cavity and wherein the controller determines the cardiac demand at least partially in accordance with a bearing indicator at least partially indicative of operation of the magnetic bearing.

In one embodiment the controller: monitors changes in the bearing indicator in response to a perturbation in blood flow, the changes being at least partially indicative of cardiac demand; and, controls the drive to thereby selectively change a rotational speed of the impeller at least partially in accordance with changes in the bearing indicator.

In one broad form, one aspect of the invention seeks to provide a controller for a heart pump, the controller including an electronic processing device that: monitors operating parameters of the heart pump to detect a trigger; and, at least one of: in response to detection of a trigger, controls a drive to rotate an impeller at a set rotational speed; and, in response to no detection of a trigger, controls the drive to rotate the impeller at a target rotational speed determined at least partially in accordance with a cardiac demand.

In one broad form, one aspect of the invention seeks to provide a method for controlling a heart pump, the method including: monitoring operating parameters of the heart pump to detect a trigger; and, at least one of: in response to detection of a trigger, controlling a drive to rotate an impeller at a set rotational speed; and, in response to no detection of a trigger, controlling the drive to rotate the impeller at a target rotational speed determined at least partially in accordance with a cardiac demand.

It will be appreciated that the broad forms of the invention and their respective features can be used in conjunction and/or independently, and reference to separate broad forms in not intended to be limiting.

BRIEF DESCRIPTION OF THE DRAWINGS

Various examples and embodiments of the present invention will now be described with reference to the accompanying drawings, in which: —

FIGS. 3A and 3B are graphs showing measured atrial pressures and corresponding bearing currents respectively measured during an animal trial;

FIGS. 6A and 6B are graphs of example rotational speed perturbations;

FIG. 9A is a graph of an example of an impeller rotational speed profile used to induce a washout pulse;

FIG. 9B is a graph of a systemic blood flow rate for the impeller rotational speeds of FIG. 9A;

FIG. 9C is a graph of a pulmonary blood flow rate for the impeller rotational speeds of FIG. 9A;

FIG. 13E is a graph of an example of changes in impeller rotational speed in response to changes in cardiac demand;

FIG. 13F is a graph of an example of changes in pulse magnitude in response to changes in cardiac demand;

FIG. 13G is a graph of an example of changes in pulse frequency in response to changes in cardiac demand;

DETAILED DESCRIPTION OF THE PREFERRED EMBODIMENTS

Figure 1A:
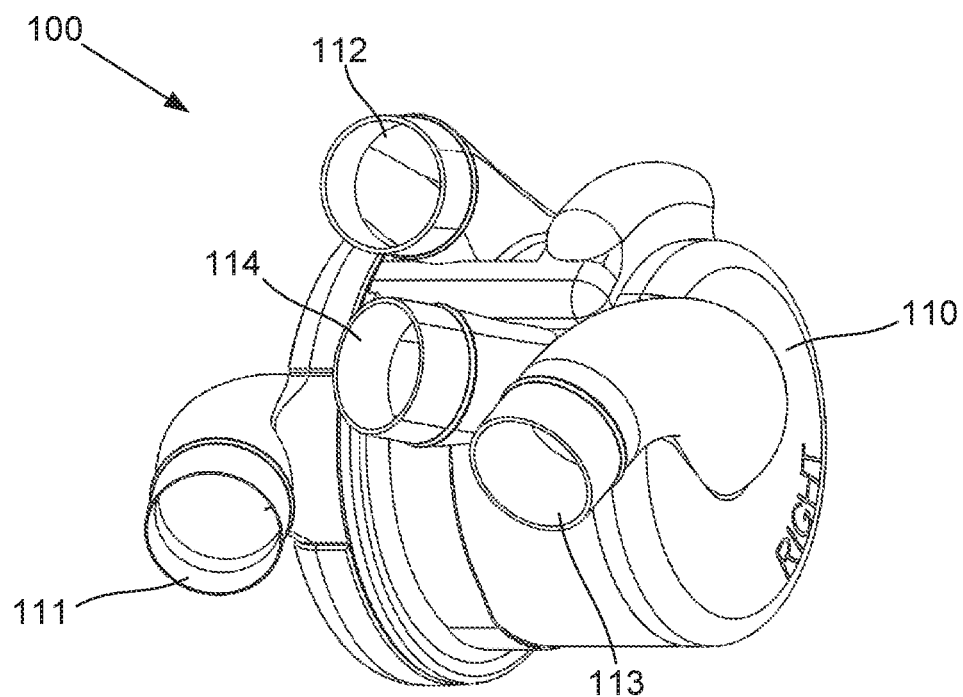
FIG. 1A is a schematic perspective view of an example of a heart pump.

An example of a heart pump will now be described with reference to FIGS. 1A to 1D.

In this example the heart pump is a biventricular device which can operate either as a ventricular assist device to assist function of left and right ventricles of a subject's heart, or alternatively as a total artificial heart. It will be appreciated however that whilst reference is made to a biventricular device this is not essential, and alternatively the control processes described herein could equally be applied to single ventricular assist devices or any form of blood pump.

In this example, the heart pump 100 includes a housing 110 defining a cavity 115. The housing can be of any suitable form but typically includes a main body 110.1, left and right end caps 110.2, 110.3 which connect to the main body 110.1, as well as an end plate 110.4 positioned between the main body 110.1 and left end cap 110.2. The housing can be made of any suitable biocompatible material, and can be made of titanium, a polymer or the like.

The housing 110 includes two inlets 111, 113, for connection to the pulmonary vein and vena cava, or left and right ventricles, and two outlets 112, 114 for connection to the aorta and pulmonary artery, respectively. Whilst two inlets and outlets are shown, it will be appreciated that this is in the context of a biventricular device, and that a single inlet and outlet can be used for a single ventricular device.

The heart pump 100 includes an impeller 120 provided within the cavity 115. The impeller 120 includes a rotor 121 having vanes mounted thereon for urging fluid from the inlet to the outlet upon rotation of the impeller 120. In this example, as the heart pump 100 is a biventricular device, the impeller includes two sets of vanes 122, 123 each of which is used for urging fluid from a respective inlet 111, 113 to a respective outlet 112, 114. In this example, the rotor 121 is positioned within the cavity 115 to effectively divide the cavity into first and second cavity portions, each having a respective inlet and outlet, thereby allowing each to function as a respective pump.

Figure 1B:
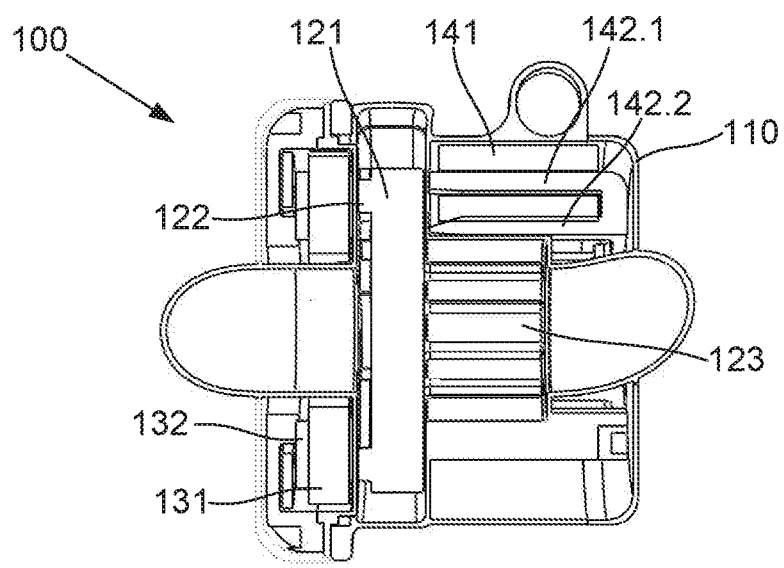
FIG. 1B is a schematic cutaway view of the heart pump of FIG. 1A.
Figure 1C:
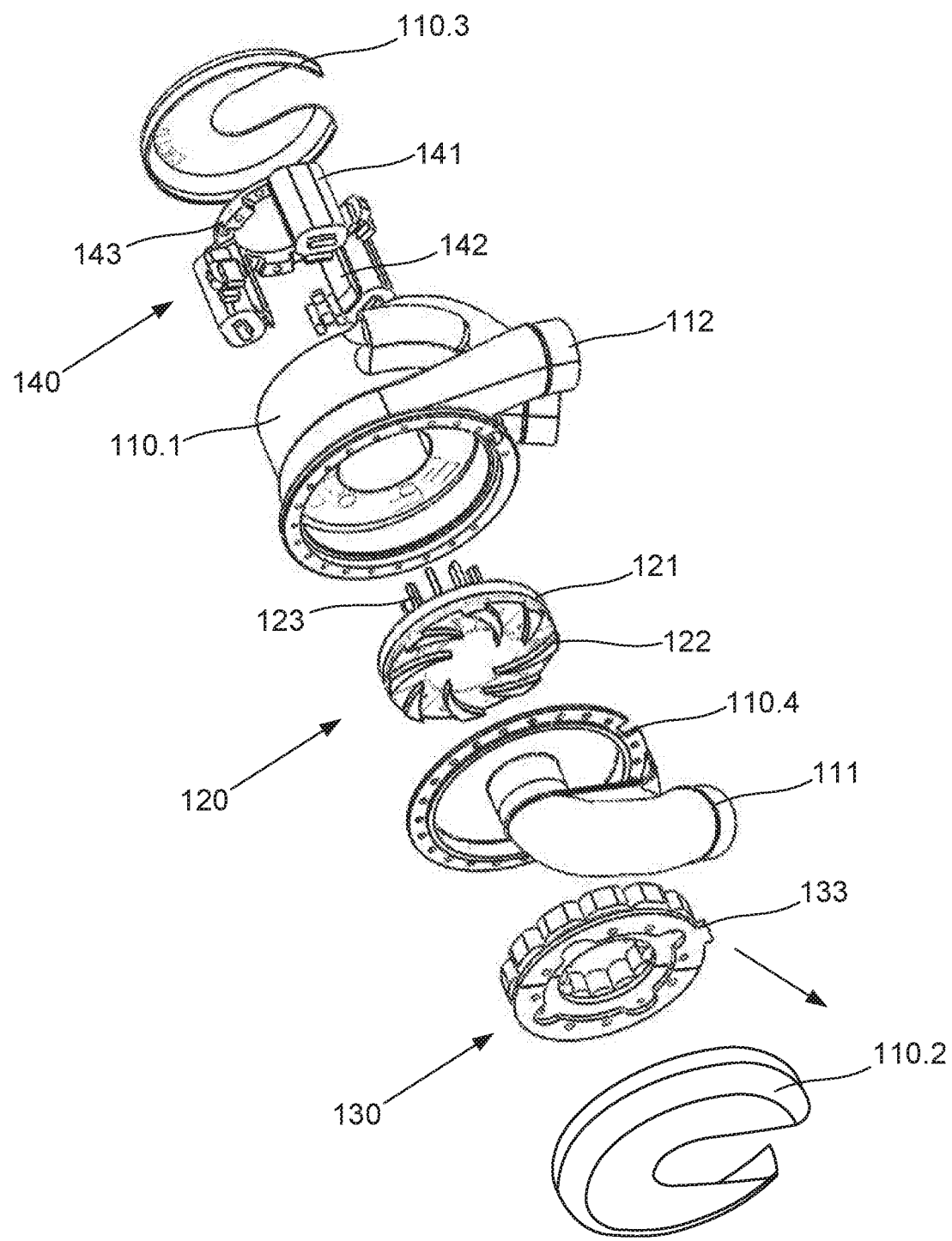
FIG. 1C is a schematic perspective exploded view of the heart pump of FIG. 1A.

Thus, in the current example, the vanes 122 are used to urge fluid from the inlet 111 to the outlet 112, with this being provided on the left-hand side of the pump in the orientation shown in FIG. 1B, and operating to provide left-ventricular function, whilst the vanes 123 urge fluid from the inlet 113 to the outlet 114 and act to provide right-ventricular function. In this context the first and second cavity portions are generally referred to as left and right cavities, respectively. It will be appreciated that in this regard, the terms left and right refer to the intended ventricular function of the cavities as opposed to the particular orientation of the pump in FIG. 1B, which is used for illustrative purposes only.

The heart pump 100 further includes a drive 130 that rotates the impeller 120 within the cavity 115. The drive 130 can be of any appropriate form but typically includes a number of coils 131 wound on a stator 132, supported by a mounting 133, allowing the drive 130 to be coupled to the housing 110. The drive cooperates with magnetic material 134 mounted in the rotor 121 with this typically being in the form of a number of circumferentially spaced permanent magnets mounted in the rotor 121 proximate an outer circumferential edge of the rotor and proximate a face of the rotor facing the drive coils 131. In one specific example, the coils 131 and stators 132 are wedge shaped and circumferentially spaced around the mounting 133, so as to provide twelve electromagnets radially aligned with circumferentially spaced drive magnets 134 in the rotor 121, to thereby maximise a degree of magnetic coupling between the magnets in the rotor 121 and the drive 130. The drive magnets 134 are typically arcuate shaped rare earth magnets, circumferentially spaced proximate an outer circumferential edge of the rotor 121, and mounted on a soft iron rotor drive yoke.

The heart pump 100 can further include a magnetic bearing 140 including at least one bearing coil 141 which cooperates with bearing magnetic material mounted in the rotor 121 allowing to thereby control an axial position of the impeller 120 within the cavity 115. In one particular example, shown in more detail in FIGS. 2D to 2F, the magnetic bearing includes three bearing coils 141, each of which is mounted on a first leg 142.1 of respective U-shaped stators 142, with a second leg 142.2 being positioned radially inwardly of the first leg 142.1. The stators 142 are mounted to a support 143 and circumferentially spaced 120° apart around the housing so that the first and second legs 142.1, 142.2 align with respective magnetic material, such as bearing magnets 144, 145, optionally mounted on a common yoke (not shown) allowing an axial position of the impeller 120 to be controlled.

The bearing magnetic material typically includes first and second annular magnetic bearing members mounted within and proximate a face of the rotor facing the bearing coils 141, the first magnetic bearing member being provided radially outwardly of the second magnetic bearing member. In one particular example, the first bearing magnet material 144 includes an annular soft iron material that can be integrally formed with the annular yoke, or an annular permanent magnet 144 mounted on the yoke, and mounted in the rotor, proximate an outer circumferential edge of the rotor 121. The second bearing magnetic material is an annular permanent bearing magnet 145 mounted radially inwardly of the first bearing member 144, so that the first and second bearing members 144, 145 align with respective legs 142.1, 142.2 of the stators 142. It will be appreciated the annular members could include a plurality of individual elements, such as individual circumferentially spaced magnets or ferromagnetic elements. Additionally, the use of a magnetic bearing may not be required and can be replaced by a static physical bearing, or the like.

Figure 1D:
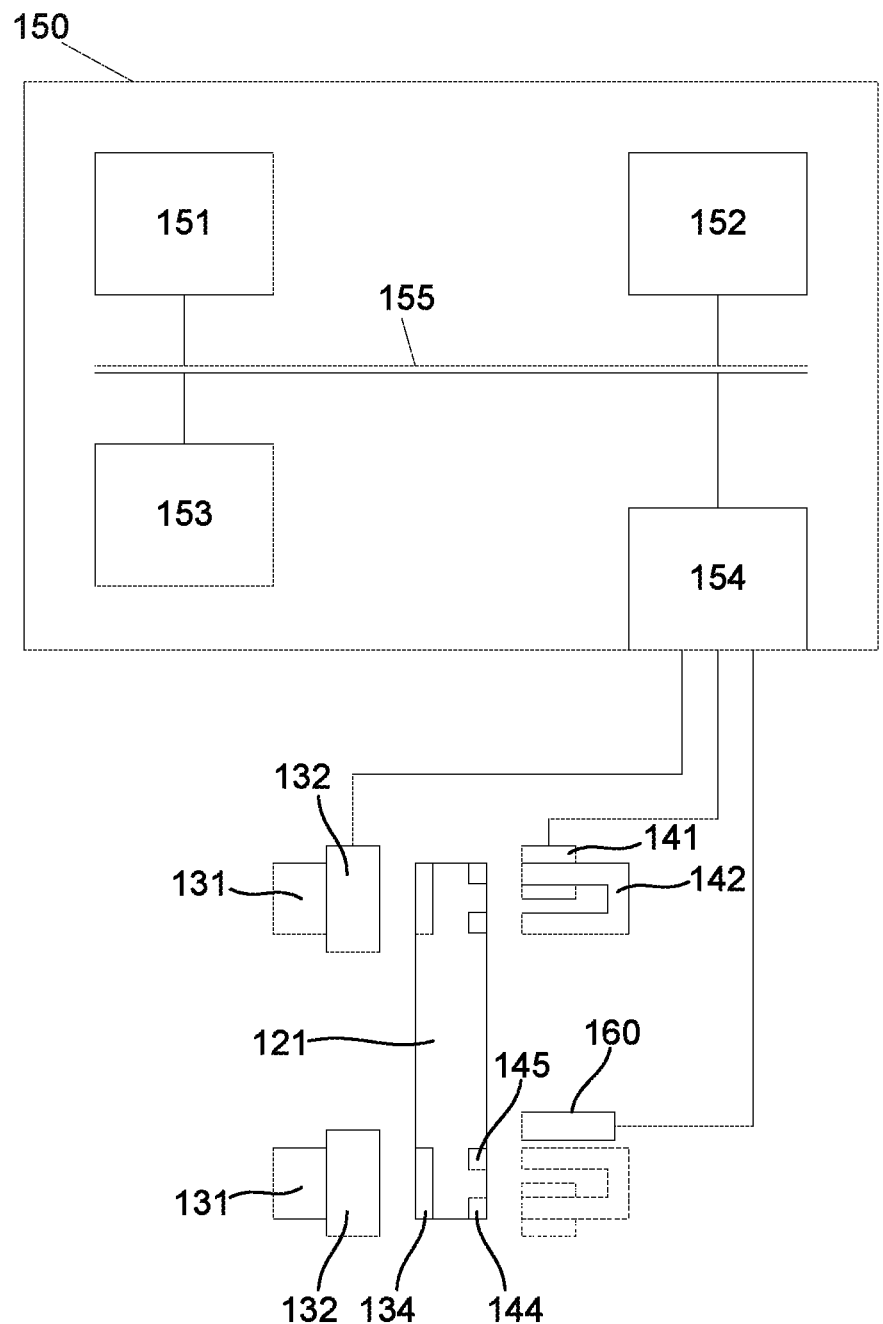
FIG. 1D is a schematic diagram of an example of a control system for the heart pump of FIG. 1A.

The drive 130 and magnetic bearing 140 are mounted at opposing ends of the housing 110 so that the drive and bearing 130, 140 are provided proximate opposing surfaces of the rotor 121 as shown for example in FIG. 1D, and FIGS. 2H and 2I. In the current example the drive 130 is mounted adjacent the left pump, whilst the bearing 140 is mounted adjacent the right pump, although the opposite configuration is contemplated. The depicted arrangement has a number of benefits.

Firstly, the inherent attractive magnetic forces between the drive and rotor and the bearing and rotor can be configured to substantially balance when the rotor is provided at a balance point at a normal operating speed, which may for example by approximately at a center of the cavity under conditions of normal hemodynamic conditions.

For example, this arrangement can be configured so that the magnetic forces inherent between the drive 130 and the magnetic bearing 140 and impeller 120 are matched at an impeller balance position within the cavity, which corresponds to a desired position of the impeller under conditions of normal flow. This minimises the bearing current required to maintain the position of the impeller 120 within the cavity, hence reducing the amount power required to operate, and in particular drive and axially position the impeller.

Additionally, as well as having the magnetic forces balance, the forces generated by the drive and bearing can also be configured to provide a desired degree of axial and radial stiffness. In this regard, the stiffness is a measure of the deflection of the impeller 120 from a balance position in response to an external force. In one example, it is desirable to maximise the radial stiffness so as to maintain the impeller radially centralised within the cavity and to stop the impeller touching the inner circumferential wall of the cavity. Conversely, as the axial position of the impeller 120 can be used for flow control, and in particular to allow for passive and/or active response to changes in hemodynamic parameters, a low degree of axial stiffness is preferred. Accordingly, the passive magnetic forces can be configured to assist in meeting these requirements, as will be described in more detail below.

A further benefit of the above described arrangement, in the context of BiVAD applications, is that it allows the greater size of the magnetic bearing to be accommodated by the smaller size of the right pump cavity. In particular, this allows a gap between a bearing stator and bearing magnets to be minimized, as no vanes are located in this gap (as opposed to the left side where vanes are located in the magnetic airgap between the drive and the rotor), as will be described in more detail below. However, it will be appreciated that this limits an outer diameter of the right pump and thus achievable pressure generation at a given rotational speed, although for right pumps this is generally not an issue given their lower flow requirements than the left pump. The apparatus further includes a controller 150 which, in use, is coupled to a sensor 160 and the drive and bearing coils 131, 141. The sensor 160 senses an axial position of the impeller 120 within the cavity 115 and can be of appropriate form such as a reluctance or eddy current sensor, which detect magnetic fields within the rotor 121 to thereby determine a separation between the rotor and the sensor 160, as will be appreciated by persons skilled in the art.

Typically three sensors would be provided circumferentially spaced around the rotor. In the case of eddy current sensors 160, each sensor would typically include a coil mounted in a housing, circumferentially spaced and aligned with the inner leg 142.2 of the magnetic bearing stators 142. The coil is aligned with a rotor shell/target mounted radially inwardly of a first bearing magnet 144, so as to generate a field therein, with variations in the field being detected to determine the separation of the sensor 160 and the shell/target, and hence the rotor 121. However, it will be appreciated that other suitable sensors can be used, such as reluctance sensors or the like, in which case the first permanent magnet 144 might be replaced with ferromagnetic material, depending on the sensor/bearing requirements.

In use the controller 150 is adapted to monitor signals from the position sensor 160 and then control the current supplied to the drive coils 131 to control rotation of the impeller and to the bearing coils 141 to control the axial position of the impeller 120. Thus, the impeller 120 is acted upon by the fluid pressures in the housing 110, which create a net hydraulic force on the impeller 120. Forces acting on the impeller 120 are compensated for by the magnetic bearing, with the controller 150 operating to control the amount of current supplied to the electromagnets in the bearing to thereby maintain the position of the impeller 120. As such, the current used by the magnetic bearing system has a direct correlation to the forces and pressures acting on the impeller 120. In this manner, changes to the inlet and outlet pressures can be detected through the magnetic bearing signals in real-time.

The controller 150 can be of any suitable form but typically includes an electronic processing device 151, an optional memory 152, and an interface 154 for connecting to the heart pump, each of which are interconnected by a bus 155, or other similar arrangement. The electronic processing device can be any form of electronic processing device capable of interpreting signals and causing the drive and bearing to be controlled, such as a microprocessor, microchip processor, logic gate configuration, firmware optionally associated with implementing logic such as an FPGA (Field Programmable Gate Array), or any other electronic device, system or arrangement.

An optional external interface 153 may be provided allowing for interaction with the controller 150. In the event that the controller is positioned outside the body this could include an I/O device 153 such as a touch screen or the like, whereas if positioned inside the body this would typically be in the form of a wireless communications module allowing communication with an external control device.

Figure 2:
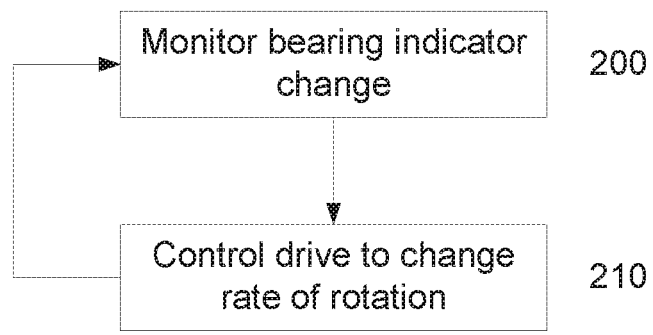
FIG. 2 is a flow chart of an example of a speed control process for use with a heart pump.

Operation of the control system of FIG. 1D to control the rotational speed of the impeller will now be described with reference to FIG. 2.

An example of a control process for controlling the rotational speed of the impeller will now be described with reference to FIG. 2.

In this example, at step 200 the controller 150 operates to detect onset of a low pressure condition, typically by monitoring changes in a bearing indicator in response to a perturbation of blood flow within the pump. The bearing indicator is at least partially indicative of operation of the magnetic bearing and can be indicative of an axial position of the impeller but more typically is indicative of a bearing power used by the magnetic bearing. In particular, the bearing power indicator is typically indicative of, or derived from, the bearing current drawn by the magnetic bearing. However, it will be appreciated that this is not essential, and any suitable bearing indicator can be used.

The perturbation in blood flow may be caused by any event and could include physiological events, such as changes in the blood pressure within a patients circulatory system, or induced perturbations caused for example by perturbing the rotational speed and or axial position of the impeller.

At step 210 the controller controls the drive 130 to thereby selectively change a rotational speed of the impeller at least partially in accordance with changes in the bearing indicator, and in one example based at least partially on onset of a low pressure condition.

Whilst a variety of different control mechanisms can be used typically the control process performed is used to attempt to maximise the rotational speed of the impeller whilst avoiding low pressure conditions such as suction events, vasculature collapse or deformation, connecting conduit collapse or deformation, or the like. In this regard, the pump inlets 111, 113 are coupled to the atrial or ventricular vasculature, which are compliant and deformable. Low or negative pressures in that vasculature region can potentially cause deformation and partial to full occlusion, leading to an increased resistance to flow into the pump, leading to a reduction in pressure at the inlet 111, 113 to the pump. Variation of the inlet or outlet pressures will result in a change in the force acting on the impeller 120.

As collapse of the vasculature occurs rapidly, onset of such low pressure conditions results in rapid changes in pressure within the cavities in the heart pump. Such rapid changes in pressure cause large net hydraulic forces to act on the impeller, which in turn causes a rapid spike in the bearing current required in order to maintain the impeller in a fixed position, or alternatively a rapid movement of the impeller within the cavity in the event that bearing current remains constant. Accordingly, monitoring changes in a bearing indicator can usefully provide an indication of the onset of such low pressure events.

In particular, with a constant pump flow, events that temporarily reduce the venous return to the atrium (such as Valsalva/straining/posture changes) will result in a net decrease to the volume in the atrium and surrounding vasculature. Due to the compliant nature of the atrium, this reduction of volume in the atrium will result in a reduction of pressure at the inlet of the device. If the volume in the inflow conduit region is high at the onset of the event the reduction in volume is enacted as a reduction in inlet pressure proportional to the compliance. If the volume in that region is low before the event occurs, the reduction of volume can cause the pressure to decrease to or beyond the critical value where the vasculature or connecting conduit begins to deform or collapse, triggering a larger change in the inlet pressure. The vasculature can return to its normal state if the pressure is increased back past the critical value either through an increase in the venous return or a decrease of pump flow. These events and their associated changes of inlet pressure will be propagated to the impeller as a change of force, which the magnetic bearing will balance through adjustment of its current or position and thus opposing magnetic force. As such, the occurrence and magnitude of the low volume state will be detectable through analysis of the magnetic bearing current signal.

In one example, when changes are small and slow, changes in impeller axial position can be used to take up the difference in force without adjusting the speed. However, if the axial position of the rotor moves to extreme position limits, the additional forces that would usually move the impeller further are then translated directly to current, and used to control the speed. In these instances, faster speed reduction occurs (since the threshold is tripped more often) which assists to return volume in the depleted chamber.

An example of this is shown in FIGS. 3A and 3B, which show variations in arterial pressure and bearing current for a calf during an animal trial.

In particular, FIG. 3A shows a range of different atrial pressures with a low pressure event being represented by the portion of the wave form shown at 301. Notably, the waveforms include peaks and troughs corresponding to perturbations in the speed of the impeller. The corresponding magnetic bearing current for each atrial pressure is shown in FIG. 3B, which as shown at 302 demonstrates significantly greater peaks and troughs for low pressure conditions that then higher pressure conditions, exemplifying that monitoring the operation of the magnetic bearing allows for detection of low pressure events to be performed. Whilst the change monitored can be an absolute change, such as a magnitude of a current required to maintain the impeller at a constant axial position within the cavity, more typically a gradient or rate of change is measured as this provides a greater indication of the onset of a low pressure condition.

Whilst detecting of low pressure events can be used in any form of control strategy, typically the controller 150 operate to maximise the rotational speed of the impeller 120 as this maximizes blood flow through the pump 100, which in turn helps ensure adequate blood flow is achieved in a range of physiological states. For example, in pumps where an impeller rotational speed is maintained at a set rate, this typically needs to be set based on rest conditions so as to ensure that flow is appropriate while the subject is at rest. However, in this instance, when the subject moves or attempts to exercise, blood flow is typically inadequate, leading to the subject rapidly feeling out of breath, tired or lightheaded. Accordingly, the ability to maximise pump speed based on current physiological conditions is important in ensuring the pump is able to function appropriately for a wide range of physiological states.

However, when running at a high rotational speed, this can lead to over-pumping, for example in the event that the subject ceases exercising and returns to a rest condition. Over-pumping can lead to emptying of the left atrium, ventricle or pulmonary vein, leading to a low pressure event, such as suction events or vasculature/conduit collapse, which is in turn problematic for circulation.

Accordingly, in one example the control process is implemented so as to attempt to continuously increase the rotational speed of the impeller up until a point at which onset of low pressure events is detected, at which point the rotational speed of the impeller is reduced by a predetermined amount. This maintains the pump operating at a maximum effective speed, ensuring that adequate blood flow is maintained for the subject's current physiological state, whilst ensuring suction or other low pressure events are avoided.

Accordingly, the above described control process can be used to operate ventricular assist or total artificial heart devices in an efficient manner in order to maximise the effectiveness of the pumping process.

A number of further features will now be described.

Whilst the above described example has focused on detecting onset of low pressure events by examining the bearing indicator, the onset can be detected in other manners, such as by monitoring an axial position of the impeller within the cavity, for example using the magnetic bearing and/or using position sensors. Additionally and/or alternatively this can be based on operation of the drive for example by monitoring the rotational speed of the impeller and/or a drive indicator at least partially indicative of operation of the drive, and examples will be described in more detail below.

The bearing indicator is typically indicative of an electrical current used by the magnetic bearing but could additionally or alternatively be indicative of another aspect of operation of the bearing, such as a tilt of the impeller relative to the bearing and/or an axial position of the impeller within the cavity, depending upon the control strategy used by the heart pump. As previously mentioned, the bearing indicator can be simply indicative of a change in indicator, and hence either a change in tilt, electrical current or axial position of the impeller, but more typically is indicative of a derivative or rate of change, as this provides greater sensitivity to the onset of low pressure events. The bearing indicator could also be based on multiple degrees of freedom, such as the tilt and the impeller axial position.

In order to detect a low pressure event the controller 150 typically compares the change in bearing indicator to a bearing threshold and then controls the rotational speed in response to results of the comparison. In particular, the controller 150 typically selectively decreases the rotational speed of the impeller 120 in response to the change in bearing indicator exceeding the bearing threshold, which is indicative of onset of low pressure event, or selectively increases the rotational speed of the impeller 120 in response to change in the bearing indicator not exceeding the bearing threshold, thereby maximising the rotational speed of the impeller 120 up until a point at which onset of low pressure events is detected.

Whilst a single threshold may be implemented, more typically the controller 150 compares the bearing indicator to multiple bearing thresholds and controls the rotational speed in response to the results of the comparison. Multiple thresholds can be used allowing changes in the rotational speed of the impeller to be increased or decreased in greater increments, depending upon the change in bearing indicator. Thus for example if the rate of change is relatively low, this indicates that the pump is operating at a point well away from the onset of low pressure events in which case the pump speed can be increased by a greater amount then if the rate of change of bearing indicator is high indicating onset of low pressure events is near.

The controller 150 can also be adapted to determine a number of successive rotational speed changes, compare the number to a threshold and then adjust the bearing thresholds in response to results of the comparison. Thus, if the pump speed has been increased ten times in a row, the bearing threshold can be altered in order to control the likelihood or magnitude of a further increase in pump speed.

The controller 150 typically operates to monitor the bearing indicator over a set time period and then determines a maximum change in bearing indicator during the set time period with this being compared to the bearing threshold.

As mentioned above, the change in bearing indicator is typically indicative of a low pressure event corresponding to one or more of a section event, vasculature/connection conduit collapse or vasculature defamation. Alternatively, the change in bearing indicator can be defined to correspond to a set blood pressure which can be greater than the onset of a low pressure event, thereby helping further avoid low pressure events.

It will also be appreciated however that other operational characteristics of the pump can have an impact on the bearing indicator. For example, if the pump is operated with a varying rotation speed, for example to simulate a physiological pulse, a large pulse can result in change in bearing indicator that is similar to that indicative of onset of a low pressure event without a pulse occurring.

Accordingly, in one example, the controller can select the bearing threshold based on a drive indicator at least partially indicative of operation of the drive. In this example, the threshold can be changed dynamically as the drive is controlled, to thereby help reduce false positives in detecting the onset of low pressure events. This is particularly useful when the pump is operated in a pulsatile mode, for example to produce a washout pulse or simulate a physiological, as will be described in more detail below. In this instance, the threshold can be set based on the magnitude of the pulse, to thereby prevent the pulse triggering a false positive result. Alternatively, an amplitude of the pulse can be set based on the threshold, again ensuring the pulse does not generate a false positive.

The bearing threshold could alternatively be set based on other operating characteristics, such as a position of the impeller within the cavity. For example if the hemodynamics cause the impeller to move towards the right cavity, the threshold may be different compared to if the hemodynamics cause the impeller to move to the left cavity. This approach can be implemented in any suitable manner, and could include for example, dividing the cavity into discrete regions, varying the threshold continuously over the entire cavity. The signal used to determine the threshold might also be a low pass filtered version of the position (to try and smooth out the impeller movement), or could also be the impeller position immediately prior or after a pulse. For example at the start of the pulse (end of diastolic period) the impeller position can be used to determine the current state of the system and how much capacity there is in the system to potentially pulse or to evaluate a suction event.

In another example, the controller can determine an indicator at least in part using a drive indicator which is at least partially indicative of operation of the drive. In this regard, partial and full suction events reduce the flow through the pump due to the increased resistance. This reduction in flow reduces the torque required by motor and consequently the power.

In this example, the drive indicator can be indicative of any aspect of drive operation and could include a current supplied to the drive, an expected rotational speed of the impeller, an actual rotational speed of the impeller and a magnitude of a rotational speed change.

Whilst the drive indicator alone can be used, when drive and bearing indicators are combined this decrease in torque during partial and full suction can be used to amplify the feedbacks signal. Furthermore, due to the compliant nature of the physical system there may be delays between the motor signals and the MB signal event. As such, delays of the signals can be made to help align the critical events.

In one example, this is achieved by having the controller determine a combined indicator based on a combination of the bearing indicator and a drive indicator which is at least partially indicative of operation of the drive. In this example, the combined indicator can be based on any suitable combination of the drive and bearing indicators, including but not limited to multiplying the bearing and motor indicators, dividing the bearing and motor indicators, determining a ratio of the bearing and motor indicators, adding the bearing and motor indicators, subtracting the bearing and motor indicators, determining a weighted sum of the bearing and motor indicators, determining a log sum of the bearing and motor indicators, determining a weighted integral of bearing and motor signals and determining a convolution of the bearing and motor indicators. This allows a single indicator to be derived taking into account the operation of both the bearing and the drive, in turn allowing this to be used to more accurately detect the onset of low pressure events.

Having determined the combined indicator, the control selectively changes a rotational speed of the impeller at least partially in accordance with the combined indicator. To achieve this, the controller typically compares a change in the combined indicator to a combined indicator threshold and controls the rotational speed in response to results of the comparison.

In one specific example, a combined indicator was determined using the bearing indicator divided by the drive indicator. In an animal trial this increased the linear correlation between the feedback value and the left atrial pressure, making it easier to select a threshold. Thus, stronger suction events are amplified, allowing the controller to reduce speed faster and be more sensitive to higher suction events, whilst also allowing operation of the motor to be accommodated, so that pulsing or other similar speed variations do not lead to false positives.

As previously mentioned the perturbation could include a physiological perturbation, such as a ventricular or atrial heartbeat of a subject (ventricular contraction in the case of a ventricular assist device and atrial contraction in the case of a total artificial heart) or aspiration of a subject. Alternatively, the perturbation can be a perturbation in the operation of the pump, such as a change in pump rotational speed or a change in axial position of the impeller 120.

In one particular example the controller 150 controls the drive to periodically alter the rotational speed of the impeller and thereby cause the perturbation. This can be achieved by superposing a modulated signal, such as a sinewave, squarewave, using a look-up table, or the like, on to the signal used to control operation of the drive 130. In this example, the controller 150 typically monitors changes in the bearing indicator at least partially in accordance with the frequency and profile of the perturbations. Thus, this allows signal processing techniques to be performed so that changes in bearing current are examined in conjunction with changes in the rotational speed of the impeller 120.

Thus, periodic events that naturally perturb the inflow system, such as breathing and atrial contraction, can repetitiously reduce and add volume to the atrium. If the periodic events trigger a low volume state and the associated exaggerated pressure drop with each cycle then it can be concluded that the atrial volume is low and the pump rotational speed and thus outflow is too high.

In one example, the controller controls the drive to selectively change a rotational speed of the impeller and thereby vary a blood flow rate through the heart pump to thereby induce at least one pulse. The pulse can be either a pulse adapted to simulate a natural heartbeat, or alternatively can be a washout pulse, used to flush the heart pump. The pulses can be generated in addition to the perturbation, or may be used to provide the perturbation, depending on the preferred implementation.

Generating a heartbeat pulse can be beneficial from a physiological perspective, as this allows the circulatory system to function under more normal conditions, whilst a washout pulse can be used to reduce stagnation within the pump, to help reduce thrombus formation.

Additionally, pulsing can be used to assist in controlling an overall flow rate through the pump by controlling either or both of a pulse magnitude, defined by a difference between an upper and lower rotational speed, or a pulse frequency or cyclic rate. In the current described pumps, the impeller position is a function of the hemodynamics, meaning that a magnitude of the pulse can be based on the position of the impeller. For example if the impeller is pushed into the left cavity, there is potentially more capacity in the left atrium for a larger pulse. The decision on the pulse height can be made immediately prior to the pulse (end of diastole) or based on a low pass filtered version of the position signal.

In any event, operation of the heart pump to provide a pulse will be described in more detail below.

The heart pump controller can also be adapted to provide safety overrides, that override any control behaviors, such as pulsing or otherwise adjusting rotational speed of the impeller. In one example, this is achieved by having the heart pump controller monitor operating parameters of the heart pump to detect a trigger, such as adverse operation of the pump. In this case, if a trigger is detected, the controller controls the drive to rotate the impeller at a set rotational speed, which in one example is a speed defined by an operator. Alternatively, if no trigger is detected, the controller can control the drive to rotate the impeller at a target rotational speed determined at least partially in accordance with a cardiac demand, determined for example using the bearing indicator.

Thus, this allows the pump to operate based on cardiac demand in normal circumstances and revert to a fixed speed operation in the event that an adverse condition is detected. The trigger can be based on any operating parameter of the pump, but in one example is based on an indication of the current used by the magnetic bearing, as will be described in more detail below.

Additionally and/or alternatively, detection of a trigger can be used to generate an alert, which is typically at least partially indicative of the trigger. The trigger can be of any appropriate form and could include a notification which is provided to an overseeing operator, such as a clinician, for example via a client device such as a smartphone, generating a local and/or remote visual, audible or tactile warnings, alerts or alarms or the like.

In this regard, when patient hemodynamics are outside a normal operating region (low volume, extreme SVR/PVR ratio) this tends to result in a distinctive pattern/change to the bearing indicator signals. Accordingly, detection of such events can be used to not only control operation of the pump, but also to notify relevant people regarding the situation. This can be performed in conjunction with and/or in addition to controlling operation of the pump, to ensure appropriate clinical action can be taken. This could include a medical intervention, or altering subject behaviour. For example if a patient is dehydrated which is causing a low volume state which in turn causes multiple/continued suction/speed controller events. In this case the pump could reduce the speed, but in addition the patient's fluid volume should be increased to rectify the underlining issue. In this case the controller could generate a warning or alert regarding this hemodynamic state.

Such trigger events can be detected using low-pass or band-pass signals, as described in more detail below. However, detection could also be performed using a multi factorial analysis. For example, this could include counting a number of low pressure events in a set time period, determining a number of low pressure events with the impeller in a given position, or the like.

Figure 4:
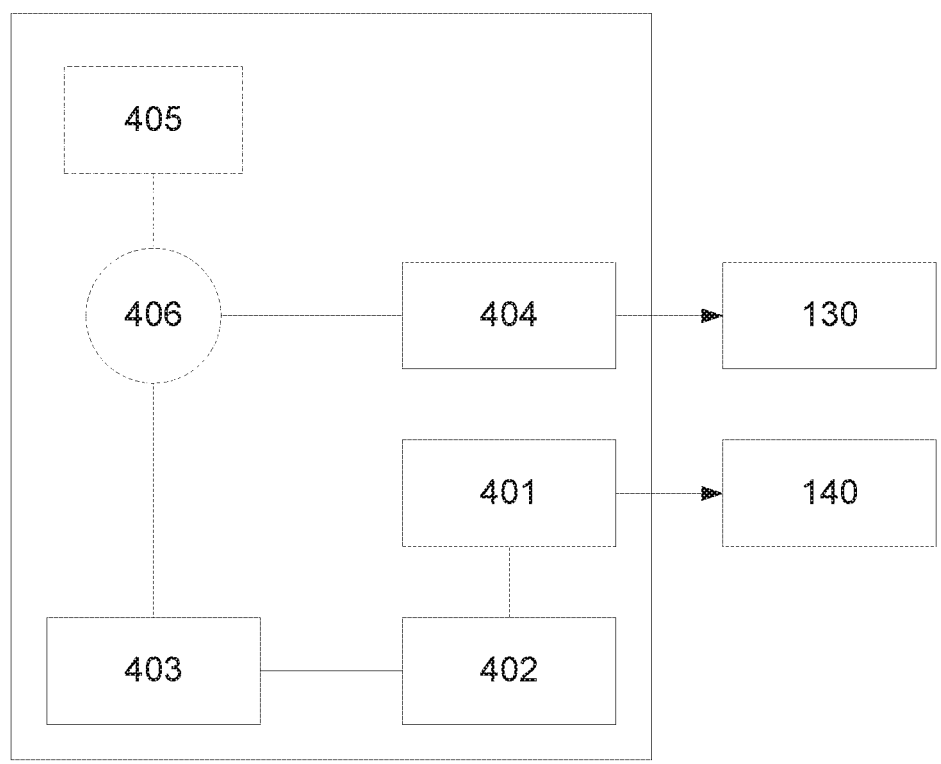
FIG. 4 is a schematic diagram of a specific example of a controller architecture.

A specific example of a controller 150 for controlling the drive 130 and bearing 140 will now be described with reference to FIG. 4.

In this example, the controller implements a bearing controller 401 which operates to maintain the impeller 120 at a target axial position within the cavity. The target axial position can be determined in accordance with zero power operations described for example in U.S. Pat. No. 8,636,638, although this is not essential and any suitable bearing control strategy can be used. However this is not essential.

In any event, the controller further includes a current sensor 402 which monitors the bearing power indicator providing any indication of this to a processor 403. The processor 403 calculates the change in required impeller rotational speed, generating a drive control, which is provided to a drive controller 404, which controls the rotational speed of the impeller accordingly. Additionally, an optional drive signal modulator 405 can be provided to generate a modulating signal for modulating the rotational speed of the impeller with this being combined with the signal output from the processor 403 by suitable logic, an amplifier or the like, at 406.

A specific example of a speed control process will now be described with reference to FIGS. 5A and 5B.

In this example the controller 150 operates to monitor the bearing indicator over a defined time window. In particular, the time window is typically defined so as to encompass a number of perturbations. For example, if the perturbations are heart beats of the subject, in the case of the heart pump being used as a ventricular assist device, then the time window would typically correspond to a number of heart beats, such as one or more beats, allowing a speed control decision to be made at the end of a respective pulse period. Typically the time window corresponds to a number of perturbations in the rotational speed of the impeller and can therefore be based on the frequency associated with a modulation signal. Alternatively the period of the time window can be made to match a single cyclic perturbation period, consequently the bearing indicator signal is evaluated for each perturbation cycle. However, it will be appreciated that the search window can be adapted to actively conform to changes in patient condition, such as variations in heart rate between when the subject is resting or exercising. Thus, the periodic search window period can also be changed while the controller is running, either by user intervention or autonomously, to adapt to a change of the perturbation function. The search windows can also be reduced in length until they are effectively continuous. The search window can also be completed prior to the predefined search time period if the bearing indicator has already exceeded the bearing threshold.

The use of a modulation of the heart pump to provide the perturbation can be advantageous as it allows a greater degree of control over the perturbation, allowing this to be taken into account when processing the changes in bearing indicator. Additionally different forms of perturbation can be used in order to maximise the impact of the perturbation on the bearing indicator, thereby making the detection process more effective. Example modulation signals are shown in FIG. 6A, which shows a sinewave modulation, or FIG. 6B which shows squarewave modulation. Additionally, as shown in FIG. 6B, the magnitude of the perturbation need not be constant, and it will be appreciated that other parameters can be modified, for example by varying frequency, amplitude, or relative duration of higher rotational speed portions with respect to the total period. It will be appreciated from this that any form of modulation can be used and that the examples shown are not intended to be limiting.

At step 505 the controller 150 determines a maximum derivative signal. Determination of the derivative can be achieved in any one of a number of ways such as by filtering the bearing current signal measured by the current sensor 402, using a suitable filter such as a band-pass filter, as will be appreciated by persons skilled in the art. The maximum derivative signal, corresponding to the greatest rate of change in bearing indicator for the window is then selected.

At step 510 the controller 150, and in particular the processor 403, operates to compare the maximum derivative signal to the bearing threshold. As part of this, the threshold and/or derivative signal can be scaled to take into account a magnitude of the applied perturbation, thereby preventing a spurious result arising as a result of an excessive perturbation. The bearing threshold can be a single threshold, or alternatively could include multiple thresholds, each of which corresponds to a respective change in rotational speed. The thresholds can be fixed or determined adaptively, either based on user input commands, or previously measured responses to perturbations.

It is determined if the threshold is exceeded at step 515, and if not this is indicative that the pump is not operating at the limit of a low pressure event, and an increased rotational rate 520 of the impeller 120 is determined. Otherwise, if the threshold is exceeded, this is indicative of a low pressure event, and a lower rotational rate of the impeller 120 is determined at step 525. In this regard, it will be appreciated that the magnitude of the speed change can be a set amount, or can be determined based on the current speed, for example to increase/decrease the pump speed by a set percentage, or can be determined based on the bearing indicator comparison to the threshold. Thus, if a first threshold is exceeded, this correspond to a 25 RPM increase in rotational speed, whereas if a second threshold is exceeded, this could correspond to a 50 RPM increase in rotational speed. In addition to speed changes based on discrete thresholds, the increase of speed can be determined by a mathematical equation, such as a proportional correlational, in relation to the difference between the bearing indicator and a threshold value. The speed changes could also be based on variable thresholds, set for example based on a rotational speed or speed change of the pump.

Following this the determined new speed is compared to a defined operating range at step 530, to determine if newly determined rotational speed is within range. In particular, the pump will typically have a defined operating range corresponding to maximum and/or minimum rotational speeds that can be safely used. If the new speed is not within the range, the previous rotational speed is maintained at step 540, with the process returning to step 500 to monitor the bearing indicator over a new window. Otherwise at step 545 the speed change is implemented through appropriate control of the drive 130.

At this point, the process could return to step 500, allowing further monitoring to be performed. However, optionally at step 550, the controller 150 can determine if there has been a number of sequential speed changes (either increases or decreases), in which case the number of changes is compared to a respective threshold at step 555. If the threshold is exceeded, the bearing threshold is adjusted at step 565, for example to allow the pump rotational speed to be altered by a greater magnitude and/or to allow the comparison process to be more sensitive to the contemporary bearing indicator magnitude. Otherwise the bearing threshold is maintained and the process repeated.

Accordingly, the above described process provides a feedback mechanism, using changes in the operation of a magnetic bearing to identify the onset of low pressure events, using this information to control the speed of the impeller, typically to maximise the rotational speed of the impeller whilst ensuring that low pressure events are avoided.

The above described arrangement can be employed in wide range of circumstances and in different pump configurations. For example, this can be used when one or two pumps are used to provide assistance or replacement of the left or right ventricles, including in a TAH, when two rotary pumps to provide complete replacement of the native heart, in an LVAD/RVAD, when a single rotary pump is used to provide assistance to either the left or right ventricles, or in a BiVAD, when two rotary pumps to provide assistance to both the left or right ventricles An example of a single VAD heart pump will now be described with reference to FIGS. 7A to 7F.

In this example, the heart pump 700 includes a housing 710 defining a cavity 715. The housing can be of any suitable form but typically includes a main body, and left and right end caps which connect to the main body. The housing can be made of any suitable biocompatible material, and can be made of titanium, a polymer or the like.

The housing 710 includes an inlet 711, for connection to the left atrium/pulmonary vein or right atrium/vena cava, or left or right ventricle, and an outlet 712 for connection to the aorta or pulmonary artery, respectively.

The heart pump 700 includes an impeller 720 provided within the cavity 715. The impeller 720 includes a rotor 721 having vanes mounted thereon for urging fluid from the inlet 711 to the outlet 712 upon rotation of the impeller 720. In this example, as the heart pump 700 is a single ventricular assist device, the impeller includes a single set of vanes 722 for urging fluid from the inlet 711 to the outlet 712. In this example, the vanes 722 have a configuration similar to that described above with respect to FIGS. 11I and 11J, and these will not therefore be described in further detail, although it will be appreciated that other suitable vane configurations can be used. The impeller can also include an aperture 724 extending therethrough to allow blood to flow around the rear surface of the impeller and thereby prevent stagnation and clotting of blood within the heart pump. Furthermore, the use of a magnetic bearing in this region allows for blood gaps in excess of 200-300 μm, which can both reduces shear stress and thus red cell lysis, as well as promote greater rates of washout flow than otherwise anticipated in gaps created by hydrodynamic bearings.

The heart pump 700 further includes a drive 730 that rotates the impeller 720 within the cavity 715. The drive 730 can be of any appropriate form but typically includes a number of coils 731, each wound on a respective stator 732, supported by a mounting 733, allowing the drive 730 to be coupled to the housing 710. The drive cooperates with magnetic material 734 mounted in the rotor 721, with the magnetic material being in the form of a number of circumferentially spaced permanent drive magnets arranged proximate an outer circumferential edge of the rotor 721. In one example, the coils 731 and stators 732 are wedge shaped and circumferentially spaced around the mounting 733, so as to provide twelve electromagnets radially aligned with the drive magnets 734 in the rotor 721, to thereby maximise a degree of magnetic coupling between the magnets in the rotor 721 and the drive 730.

The heart pump 700 can further include a magnetic bearing 740 including at least one bearing coil 141 that controls an axial position of the impeller within the cavity 715. In one particular example, shown in more detail in FIG. 7E, the magnetic bearing includes three bearing coils 741, each of which is mounted on a first leg 742.1 of respective U-shaped stators 742, with a second leg 742.2 being positioned radially inwardly of the first leg 742.1. The stators 742 are mounted to or integrally formed with a support 743 and circumferentially spaced 70° apart around the housing so that the first and second legs 742.1 742.2 align with respective magnetic material, such as bearing magnets 744, 745 within the impeller 720, allowing an axial position of the impeller 720 to be controlled.

In one particular example, the bearing rotor assembly includes ferromagnetic core target 744 mounted in the rotor, proximate an outer circumferential edge of the rotor 721, and a permanent bearing magnet or ferromagnetic material 745 mounted radially inwardly of the first ferromagnetic core target 744, so that the ferromagnetic core target and bearing magnets 744, 745 align with respective legs 742.1, 742.2 of the stators 742. The ferromagnetic core target can be replaced with a second permanent magnet. However, the use of a magnetic bearing may not be required and can be replaced by a static physical bearing or hydrodynamic bearing, or the like.

Figure 7A:
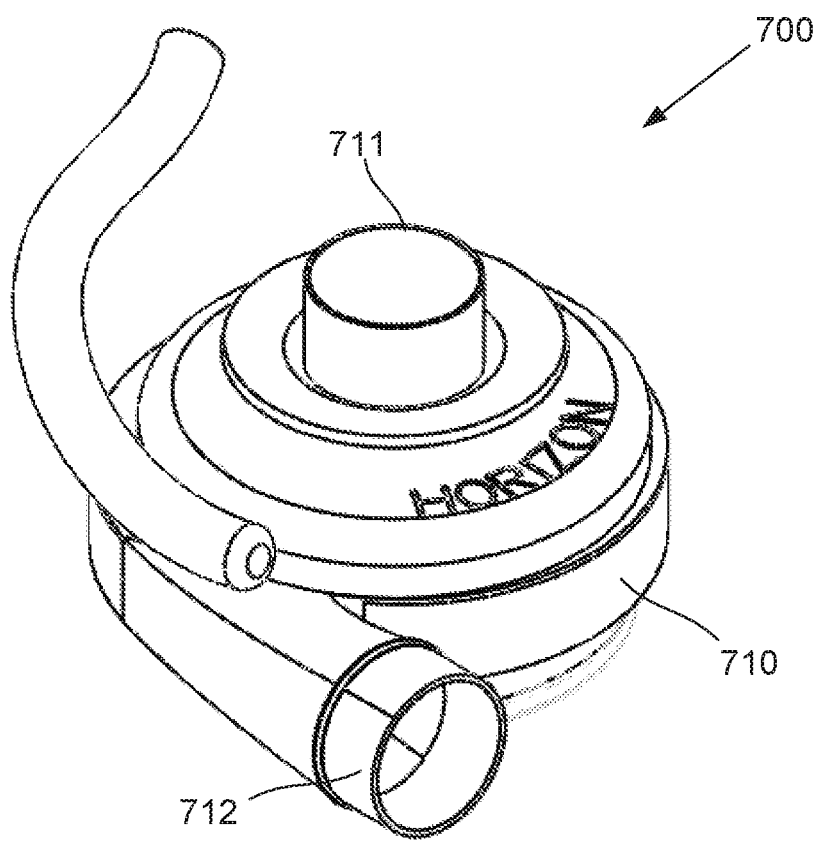
FIG. 7A is a schematic perspective view of an example of a single VAD heart pump.
Figure 7B:
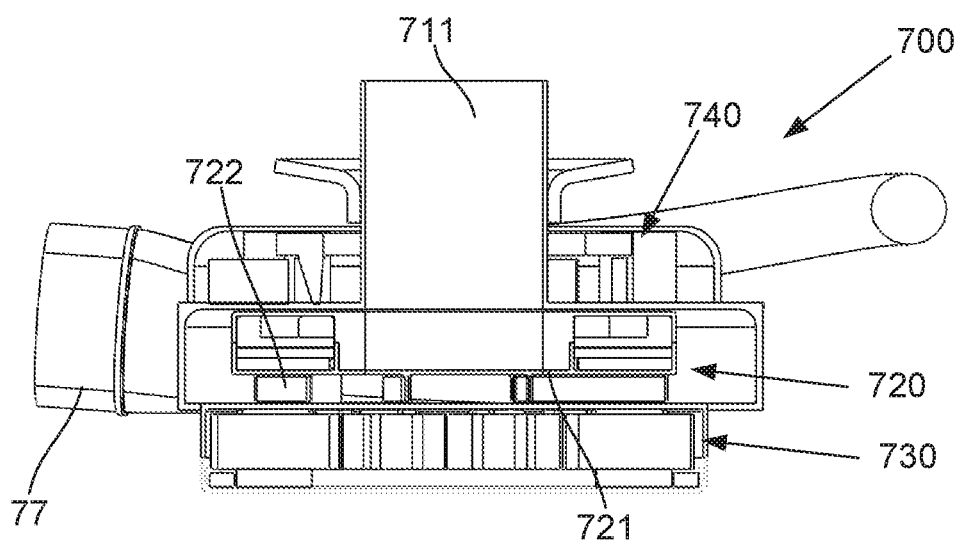
FIG. 7B is a schematic cutaway side view of the heart pump of FIG. 7A.
Figure 7C:
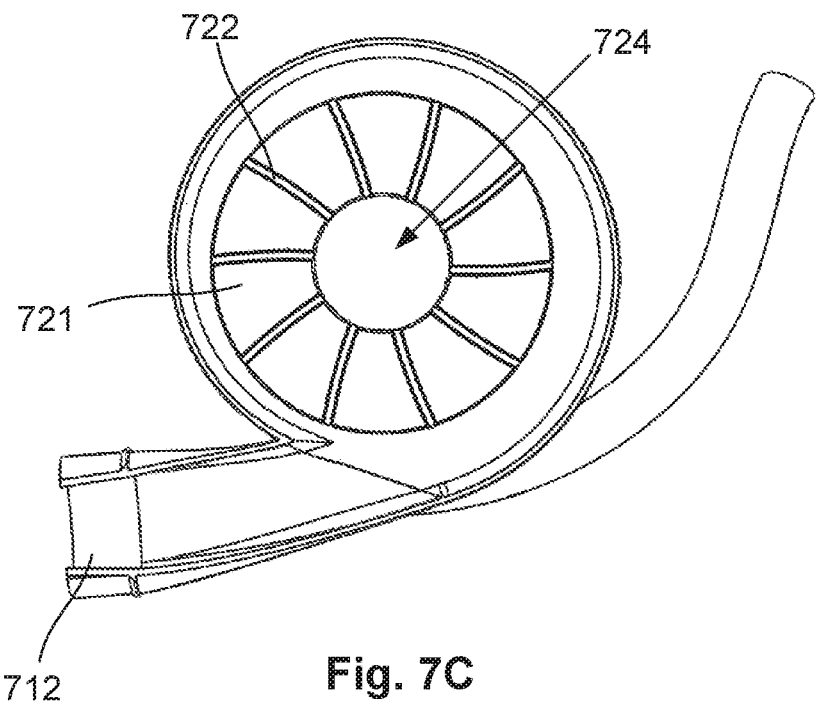
FIG. 7C is a schematic cutaway plan view of the heart pump of FIG. 7A.
Figure 7D:
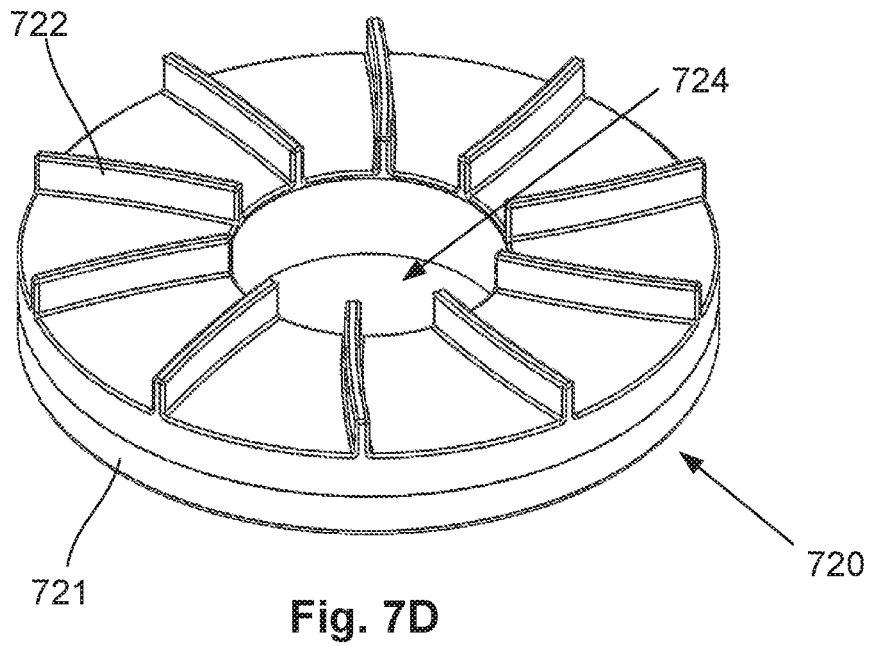
FIG. 7D is a schematic perspective view of the impeller of the heart pump of FIG. 7A.
Figure 7E:
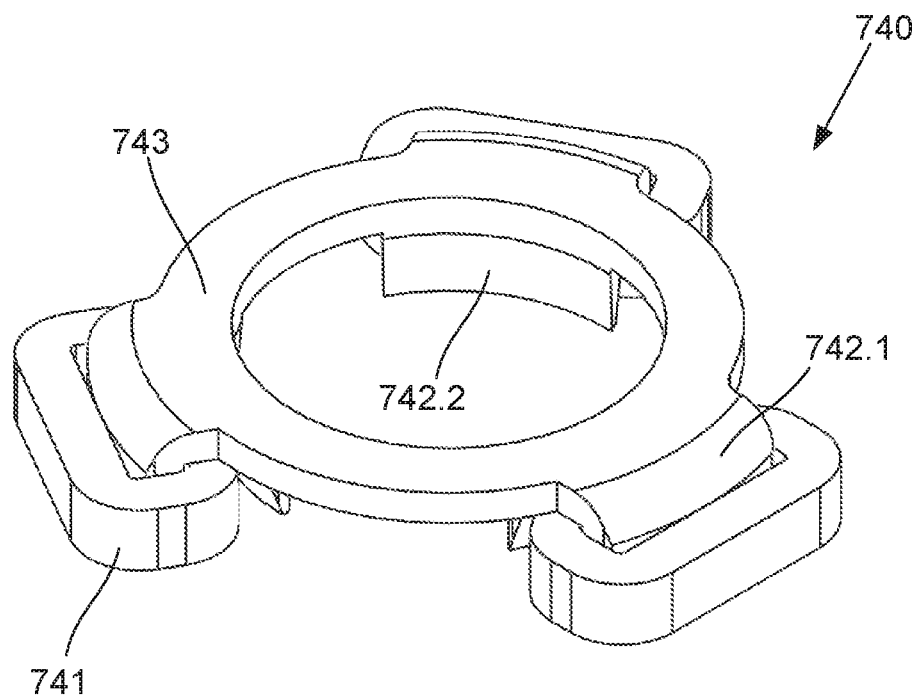
FIG. 7E is a schematic perspective view of the magnetic bearing of the heart pump of FIG. 7A; and, FIG. 7F is a schematic cutaway perspective view of the impeller of FIG. 7A.
Figure 7F:
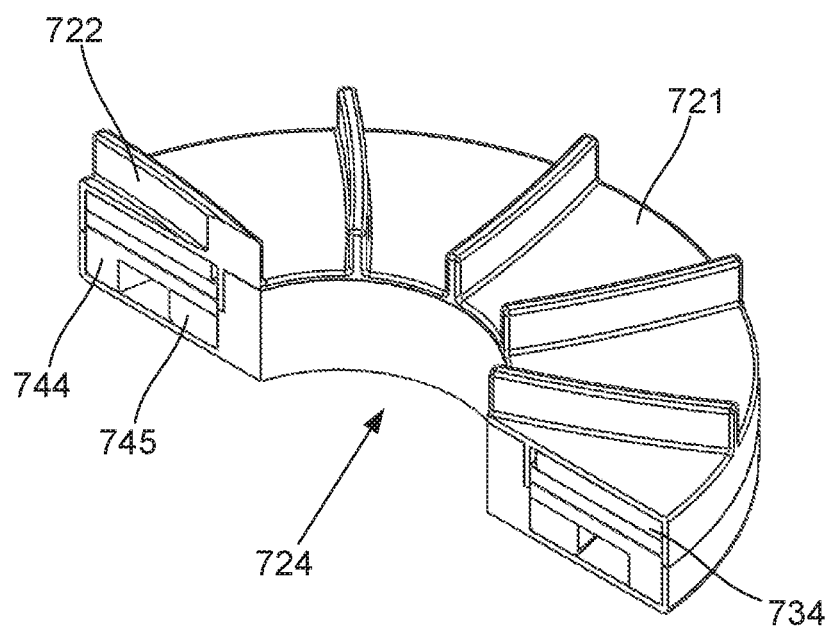

In this example, the drive 730 and magnetic bearing 740 are mounted at opposing ends of the housing 710 so that the drive and bearing 730, 740 are provided proximate opposing surfaces of the rotor 721 as shown for example in FIG. 7B. In the current example the drive 730 is mounted adjacent the side of the impeller 720 that includes vanes so as to maximise the blood gap between the rotor, vanes and the casing. That is to say, only the vane tips are in closer proximity to the casing, however this blood gap can still be in the order of 200-300 μm. Additionally, bearing and drive are configured so that the magnetic forces inherent between the drive 730 and impeller 720, and between the magnetic bearing 740 and impeller 720 and the hydraulic forces on the impeller 720 define a balance position within the cavity under conditions of normal flow. This minimises the bearing current required to maintain the position of the impeller 720 within the cavity under nominal flow conditions.

It will be appreciated as in the previous example, the apparatus can further include a controller, and otherwise functions largely as previously described, and hence will not be described in further detail.

The controller and control process can be used in a device that uses an active magnetic bearing in conjunction with a zero power controller that controls the position of the rotor in response to a change of magnetic bearing current. Signal filtering techniques on the fundamental current signal with consideration to the zero power controller can return a feedback signal appropriate for use in the controller.

The periodic perturbation of the inflow system can be achieved by periodic modulation of the pump rotational speed, with a modulation signal being added to or subtracted from or otherwise combined with a baseline rotational speed signal, and provided to a motor controller. This rotational speed modulation function can utilize sinusoidal, square, and saw tooth wave, or other suitable functions, depending on the preferred implementation. Additionally and/or alternatively, if natural ventricles or atria remain and are connected to the inlet of the pump, then the natural contraction of the ventricles or atria can be used as the periodic perturbation of the inflow condition that is used by the controller. Additionally and/or alternatively the natural breathing mechanism can be used as the periodic perturbation of the inflow condition that is used by the controller.

In addition to the fixed rate and period rotational speed modulation waveforms, the rate and period of the modulation wave can be varied based on the bearing indicator signal. For example, a square wave rotational speed modulation can be used where the maximum speed of the wave peek is chosen such that it is excessively high and operation at this high speed will inevitably cause a low pressure situation after some period of time. The speed will be increased to the maximum peek speed and maintained until the bearing indicator has satisfied some threshold. Once the bearing indicator exceeds the threshold the rotational speed is reduced to the lower speed of the modulation wave and maintained for a fixed time period or until the end of the wave period. In this manner the frequency of the periodic wave and the ratio of high and low speeds during that wave period can be changed such that mean speed of the modulation wave is effectively modified. Another example of this variable period wave modulation would be a waveform that increased the speed for a fixed time and then decreased the speed for the variable amount of time based on previous values of the indicator variable. Another example of this variable period wave modulation would be a controller which monitored the time required before the bearing indicator exceeded a threshold and the amplitude and/or period of the next wave cycle was varied accordingly. In addition these periodic modulation waveforms can have a variable frequency or wave period based on the previous and/or current bearing indicator and threshold value.

The bearing system used to suspend the rotor can utilize active or passive magnetic bearings, as well as hydrodynamic bearings. This control methodology can be used with any pump that is configured such that the pressure difference over the impeller can be detected. Thus, it will be appreciated that the above described techniques can be applied in any situation in which onset of a low pressure condition can be detected. This can include sensing an axial position of the impeller within the cavity, through analysis of the bearings, either through detection of the current in the active magnetic bearings or through measurement of the rotor location with a position sensor. This measurement of pressure applied to the impeller, either through intrinsic measurement of the active magnetic bearing current or position measurement with a separate sensor, is defined as the feedback signal and is fed into a microprocessor system for analysis.

As an alternative, this can be based on a drive indicator at least partially indicative of operation of the drive, including for example an electrical current used by the drive and/or a rotational speed of the impeller. Thus, the motor power or current could also be used as the detection signal if there is a strong correlation between the change of pressure and the change of measurable motor parameters such as inductance, back-emf and efficiency. In one example, the drive and bearing indicators can be combined in order to create a combined indicator, which is then used in a similar manner to that described above with respect to the bearing indicator. In this example, the use of a combined indicator can be used to increase the effectiveness of the detection of the onset of a low pressure event, and also reduce false positive detection, for example by distinguishing changes in bearing indicator arising from changes in other operational aspects of the pump, such as pulsing.

The filter that is applied to the measured current (or equivalent), can be chosen such that it isolates the perturbation function frequency. For example if a search modulation function is applied to the pump rotational speed the filter can be designed such that it isolates that exact frequency.

The speed of the impeller can be modified discreetly at the conclusion of the search window and comparison step. However the speed can also be varied continuously throughout the search window, with a further change to the speed applied as a result of the comparison between the bearing indicator and the bearing threshold. For example a constant ramp of the speed can be applied from the start of the search window period. Once the search period is over the base speed is incremented or decremented based on the bearing indicator and threshold and the search window is started again with the ramp beginning from the new base speed. A further improvement of this method can be the premature ending of the search window and speed ramp once the bearing indicator has exceeded the threshold, even if the search window period has not been completed.

As previously mentioned, the heart pump controller can control the drive to selectively change a rotational speed of the impeller and thereby vary a blood flow rate through the heart pump. In one example, the change in rotational speed is performed so as to induce a pulsatile flow including a series of pulses, which can simulate a normal heartbeat. Examples of this will now be described in more detail with reference to FIGS. 8A to 8F.

In particular, it is well understood that an increase in the rotational speed of the impeller, will in turn lead to a corresponding increase in blood flow through the pump, and hence to a corresponding increase in blood pressure within the systemic and pulmonary circulatory systems for left and right pumps respectively.

Accordingly, it will be appreciated that modulating the pump speed can allow a pulse of increased flow and hence pressure to be generated, which can in turn be used to mimic the pulse generated by the human heart. There are a number of reasons for doing this, primarily to subject the circulatory system to conditions that most closely resemble their natural state of operation. In particular, pulsing can help ensure adequate flow throughout the circulatory system, and allows the arteries and veins opportunity to expand and relax, which can be important to prevent blood vessel rupture.

Thus, speed modulation can be used to modulate the blood output to imitate the pulse of the native human heart. Studies indicate potential benefits of this can include Baroreceptor stimulation (improve arterial pressure regulation), possible mitigation of adverse events (Gastrointestinal bleeding, Vascular malformations), pump washout (mitigate danger of pump thrombus), including washout of the inflow and outflow conduits, improved end-organ perfusion, and for VAD operation, ventricular washout, valve stenosis and regurgitation.

It is further hypothesized that some aspects of pressure/flow waveforms are more important than others, with the more important including a high positive rate of change of pressure (dP/dt) to stretch aorta and stimulate baroreflex, high Surplus hemodynamic energy (a measure of transferred pulsatile energy) and high pump efficiency.

The aortic pressure demonstrates a distinct shape including having the pressure rise from a baseline to a first peak during systole, with a slight decrease in pressure occurring until the aortic valve closes, at which point a subsequent second minor peak occurs, with the pressure then dropping to a baseline during diastole. Accordingly, it is desirable to control the impeller rotational speed to produce a similar pressure profile.

However, additionally, it is useful to maximize the a pulse amplitude/intensity, which provides increased pulsatility with a reduced "intensity" to save power and/or impose less shear stress to the blood.

In one example, this is achieved by creating a spike in rotational speed, following this creating a first peak in rotational speed, the first peak having a magnitude smaller than the spike and then creating a second peak in rotational speed, the second peak having a magnitude smaller than the first peak.

The provision of two peaks in rotational speed, and in particular a major peak followed by a minor peak, leads to flow and pressure profiles similar to that induced by of the human heart. However, in addition to this adding a sharp spike in the speed waveform allows the rate of change in pressure over time (dP/dt) to be significantly increased, without pumping all of the blood available at the inlet, which could lead to suction.

Figure 8A:
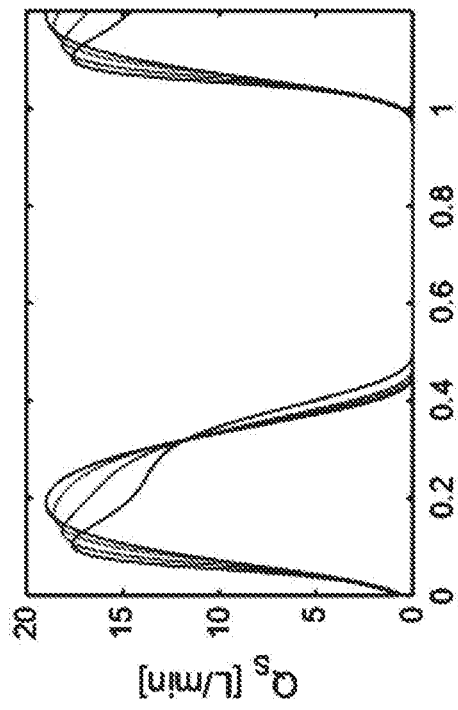
FIG. 8A is a graph of a first example of an impeller rotational speed profile used to induce a pulse.
Figure 8B:
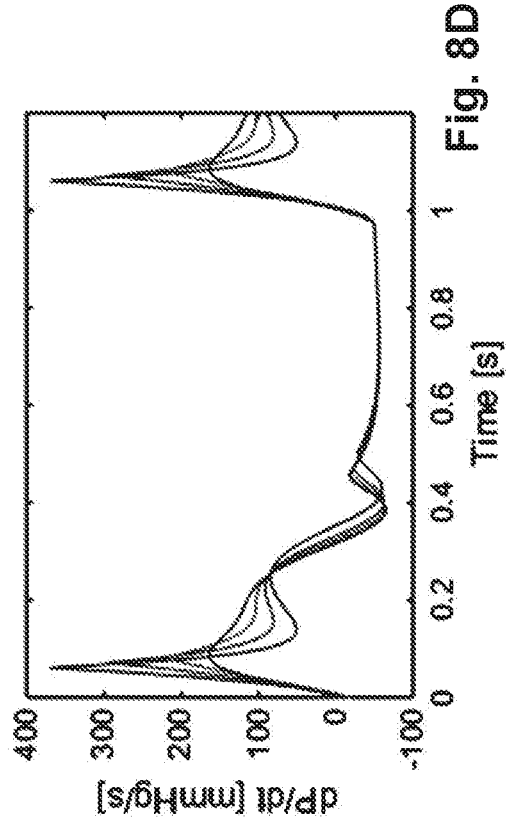
FIG. 8B is a graph of systemic blood flow rate for the impeller rotational speeds of FIG. 8A.
Figure 8C:
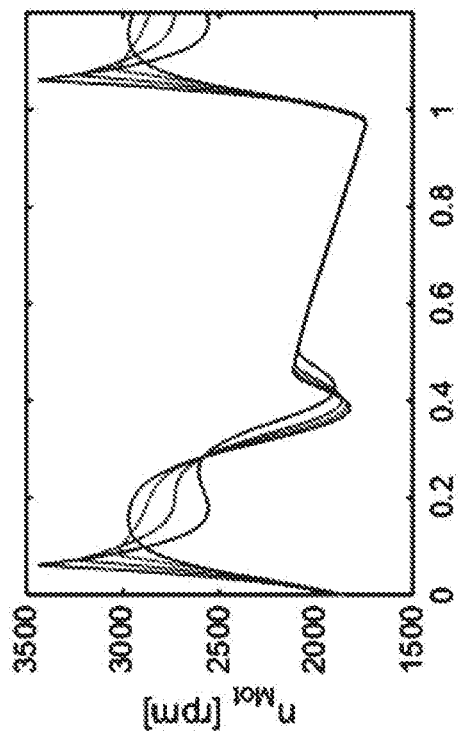
FIG. 8C is a graph of aortic blood pressure for the changes in impeller rotational speed of FIG. 8A.
Figure 8D:
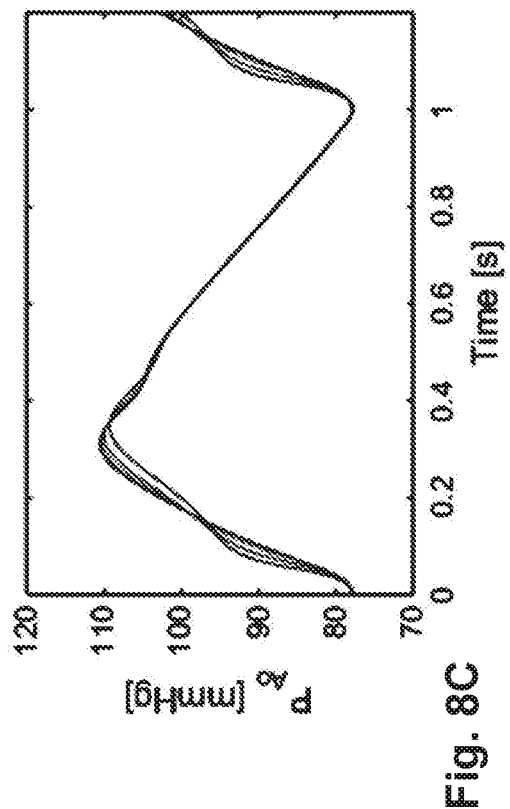
FIG. 8D is a graph of rate of change in blood pressure for the changes in impeller rotational speed of FIG. 8A.

Example rotational speed profiles are shown in FIG. 8A, with the resulting flow, pressure and rate of pressure change being shown in FIGS. 8B to 8D respectively.

A number of further features will now be described.

Changes in rotational speed lead to changes in both magnetic and hydraulic forces on the impeller, which in turn places a burden on the magnetic bearing in the event that a magnetic bearing is used. The changes in speed also lead to an increase in electrical energy used by the motor.

Accordingly in one example, each pulse is generated by progressively increasing the rotational speed to a first upper value before progressively reducing the rotational speed to a first lower value, thereby providing a major pulse peak. Following this, the rotational speed is progressively increased to a second upper value, the second upper value being lower than the first upper value, before being progressively reduced to a second lower value, thereby providing a minor pulse peak.

Additionally, progressively changing the speed, as opposed to a stepwise change, reduces the impact of changes in hydraulic and magnetic forces on the impeller. In particular, spreading the changes out over time, reduces the speed at which the magnetic bearing needs to respond, allowing the bearing to more easily maintain the position of the impeller, which in turn reduces overall energy usage.

In general, the profiles include a second lower value that is either approximately equal to the first lower value or slightly lower than the first lower value, although this is not essential, and the second lower value can be greater than the first lower value.

In general, a time period between the first and second upper values is less than a time period between the first and second lower values. Furthermore, typically the time taken for the rotational speed to increase to the first upper value of the current pulse is approximately a quarter of a pulse length, the time taken for the rotational speed to decrease from the first upper value to the first lower value is approximately a quarter of a pulse length and the time taken change the rotational speed to change from the first lower value to the second lower value is approximately half a pulse length. This timing effectively mimics the natural human pulse, but it will be appreciated that different timings can be used depending on the particular circumstances.

A magnitude of the spike from second peak lower value to the spike upper value is typically at least one of more than 500 rpm, more than 800 rpm, more than 1000 rpm, less than 2500 rpm, less than 2000 rpm, less than 1500 rpm and between 1000 rpm and 1500 rpm.

The magnitude of the pulse, and in particular the first major peak, is based on a difference between the first peak upper value and the first peak lower value. It will be appreciated that the magnitude of the pulse can be varied depending on the particular requirements, such as the current cardiac demand. However, this will also take into account the need to generate a sufficient flow variation to lead to a meaningful pressure change, without generating a rate of change that adversely affects the ability of the magnetic bearing to suspend the impeller. Accordingly, the magnitude of the pulse is typically more than 300 rpm, more than 400 rpm and more than 500 rpm, but less than 1000 rpm and in some cases, less than 800 rpm, less than 700 rpm or less than 600 rpm. In one example, the pulse magnitude is between 500 rpm and 600 rpm, for a normal cardiac demand.

The magnitude of the second minor peak, based on a difference between the second peak upper value and second peak lower value is typically at least one of more than 50 rpm, more than 75 rpm, more than 100 rpm, less than 250 rpm, less than 200 rpm, less than 150 rpm and between 100 rpm and 150 rpm.

The magnitude of each pulse could also be selected based on other operating characteristics of the pump, such as a bearing current and/or impeller position. For example, the impeller position depends on the hemodynamics, so controlling the pulse magnitude based on the impeller position, allows the pulse to be dynamically configured based on current hemodynamic requirements. Thus, in one example, the bearing indicator can be used to control a mean impeller rotational speed, with an amplitude of a pulse being determined by an impeller position prior to the pulse commencing.

The duration of each pulse can vary depending on cardiac demand, and desired operating characteristics. Typically however each pulse has a duration that is greater than 0.5 seconds, greater than 1.0 seconds, less than 2.0 seconds, less than 1.5 seconds and more typically between 1.0 and 1.5 seconds. The time taken for the spike is approximately 0.15 to 0.2 times a pulse length, the time taken for the first peak is approximately 0.2 to 0.25 times a pulse length and the time taken for the second peak is approximately 0.55 to 0.65 times a pulse length. However, it will be appreciated that other values can be used, depending on the size of each peak and the spike.

Pulses typically follow one another, so that the frequency is dependent on the duration. However, this is not essential and pulses can be separated by inter-pulse time period during which time the rotational speed of the impeller is substantially constant.

In one example, the controller can use the pulsing to control an overall flow rate through the pump. In this regard, the controller can control the flow rate by controlling a pulse magnitude defined by a difference between an upper and lower rotational speed and/or by controlling a pulse frequency. For example, if an increase in flow is required, this can be achieved by increasing the magnitude of the pulses or increasing a pulse frequency. However, this is not essential, and alternatively a baseline rotational speed can be adjusted.

The pulse can be generated in any appropriate manner, but in one example, a pulse profile is obtained from a look-up table, with the pulse profile defining the pulse relative to a baseline speed, for example by defining increases/decreases in impeller rotational speed relative to the baseline, either in terms of absolute changes in rotational speed, such as a set number of RPM, or as a percentage of baseline speed, for example increasing the rotation rate by 10%. It will be appreciated that this allows a baseline rotational speed to be selected based on cardiac demand, as described in more detail elsewhere in the document, with the pulse profile then being added to the baseline speed to generate control signals that are applied to the drive.

In another example, a physiological pulse is simulated by reducing a pump rotational speed relative to a baseline. In one example, this is performed to allow a baseline rotational speed to be set based on the current cardiac demand, and in particular to maximize the pump speed whilst avoiding the onset of a low pressure event. In this instance, if a pulse profile is added to the baseline speed, this can induce a low pressure event, accordingly by subtracting the pulse from the baseline speed, this prevents the low pressure event being induced by the pulse.

Figure 8E:
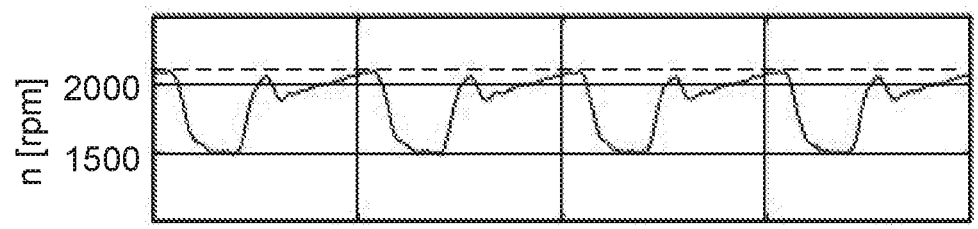
FIG. 8E is a graph of a first example of an impeller rotational speed profile used to induce a pulse.
Figure 8F:
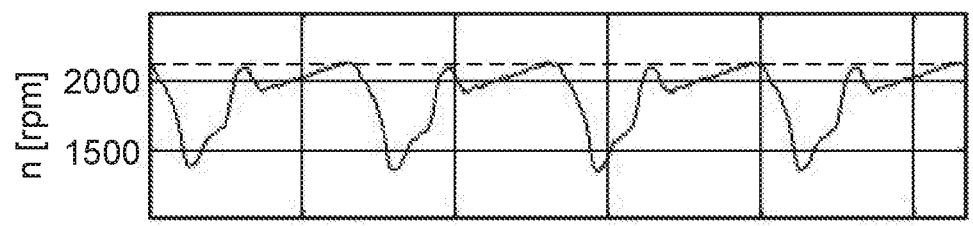
FIG. 8F is a graph of a first example of an impeller rotational speed profile used to induce a pulse.

In one example, the pulse waveform can be inverted compared to a more traditional pulse waveform. In one example, the physiological pulse waveform includes first and second troughs in rotational speed, with the first trough having a lower speed than the second trough and with the first trough being shorter than the second trough and examples of these are shown in FIGS. 8E and 8F, with the defined baseline pump speed being shown in dotted lines.

It will also be appreciated that features similar to those described above with respect to the spiked pulse profile could also be implemented. Thus, the profile could include a spike defined by a large decrease in rotational speed, followed by an increase before the first trough. The first and second troughs are typically smoothed in order to reduce energy usage.

In addition to, or as an alternative to generating a physiological pulse as described above, in one example, the controller can be adapted to control the drive to selectively change a rotational speed of the impeller, wherein the controller periodically reduces the rotational speed to below a defined threshold value to create a washout pulse.

The washout pulse is used to prevent stagnation, which in turn can lead to clotting or thrombus formation. In this regard, when operating at a constant flow rate, blood will tend to flow through the pump along defined paths resulting from the particular construction of the pump, including the size and shape of the impeller, cavities and inlets and outlets. Whilst varying the flow rate using a pulse will vary the flow paths to a degree, there is a tendency for some areas within the pump to have lower flow rates, which can lead to blood in these areas stagnating. By reducing the flow rate below a threshold amount, this sufficiently disrupts the flow, avoiding stagnation occurring. An example washout pulse is shown in FIG. 9A, with the corresponding systemic and pulmonary flow rates being shown in FIGS. 9B and 9C, respectively.

A number of further features will now be described.

The shape of the washout pulse can be of any appropriate form and in one example could include a half sinewave to minimize forces on the bearings, although other suitable shapes can be used. For example, an asymmetrical half sine wave can be used in which the rotational speed decrease has a shorter duration than the return increase in speed. When using the washout pulse, physiological pulses on either side of the washout pulse may be paused temporarily to allow flow to be in a steady state, prior to or after the washout pulse. This reduces the potential for interference between the physiological and washout pulses.

The threshold value will vary depending on factors such as the current rotation speed of the impeller and the impeller design. The threshold value is typically set so that flow through the pump substantially reduces and/or stops. In one example, the threshold value is at least one of less than 2000 rpm, less than 1900 rpm, less than 1800 rpm, less than 1700 rpm, less than 1600 rpm, more than 500 rpm less than a set operational speed, more than 600 rpm less than a set operational speed, more than 700 rpm less than a set operational speed and more than 800 rpm less than a set operational speed.

So as to minimize lack of blood flow, whilst still providing sufficient flow disruption, the washout pulse typically has a duration of at least one of at least 0.2 s, at least 0.5 s, at least 0.7 s, less than 5.0 s, less than 4.0 s, less than 3.0 s, less than 2.0 s and less than 1.0 s.

The washout pulse is typically produced with a frequency that is at least one of at least once every ten minutes, at least once every five minutes, at least once every minute, at least twice every minute and, at least five times every minute, although it will be appreciated that this may vary depending on factors such as the baseline rotational speed and the pump design. In this regard, in one example, the controller controls the drive to produce different washout pulses having a different rotational speed threshold, a different duration and/or a different frequency, to thereby maximize effectiveness.

In another example, the heart pump controller can be adapted to implement a safety protocol, to thereby maximize patient safety. In this example, the controller monitors operating parameters of the heart pump to detect a trigger and then either controls the drive to rotate the impeller at a set rotational speed in response to detection of a trigger or controls the drive to rotate the impeller at a target rotational speed determined at least partially in accordance with a cardiac demand if the trigger is not detected.

Thus, in this example, the controller monitors pump operating parameters, such as an electrical current used by the magnetic bearing, to identify circumstances which correspond to a potential risk for the patient. This can include scenarios in which the impeller is unstable, or the impeller speed or bearing is being controlled erratically, for example due to conflicting control requirements, but could also include particular physiological conditions, excessive external forces, such as impulse forces, or other situations in which there are issues, but the impeller is operating stably. In this situation, any extraneous controls, such as pulses, speed control based on cardiac demand or the like, are deactivated or reduced in magnitude, and the impeller is returned to a fixed operating speed, allowing the system to restabilise, or for any physiological conditions to clear, external forces clear, or other issues resolve. Once this has occurred controls, such as pulse or the like can be reintroduced as required.

A number of further features will now be described.

Figure 10:
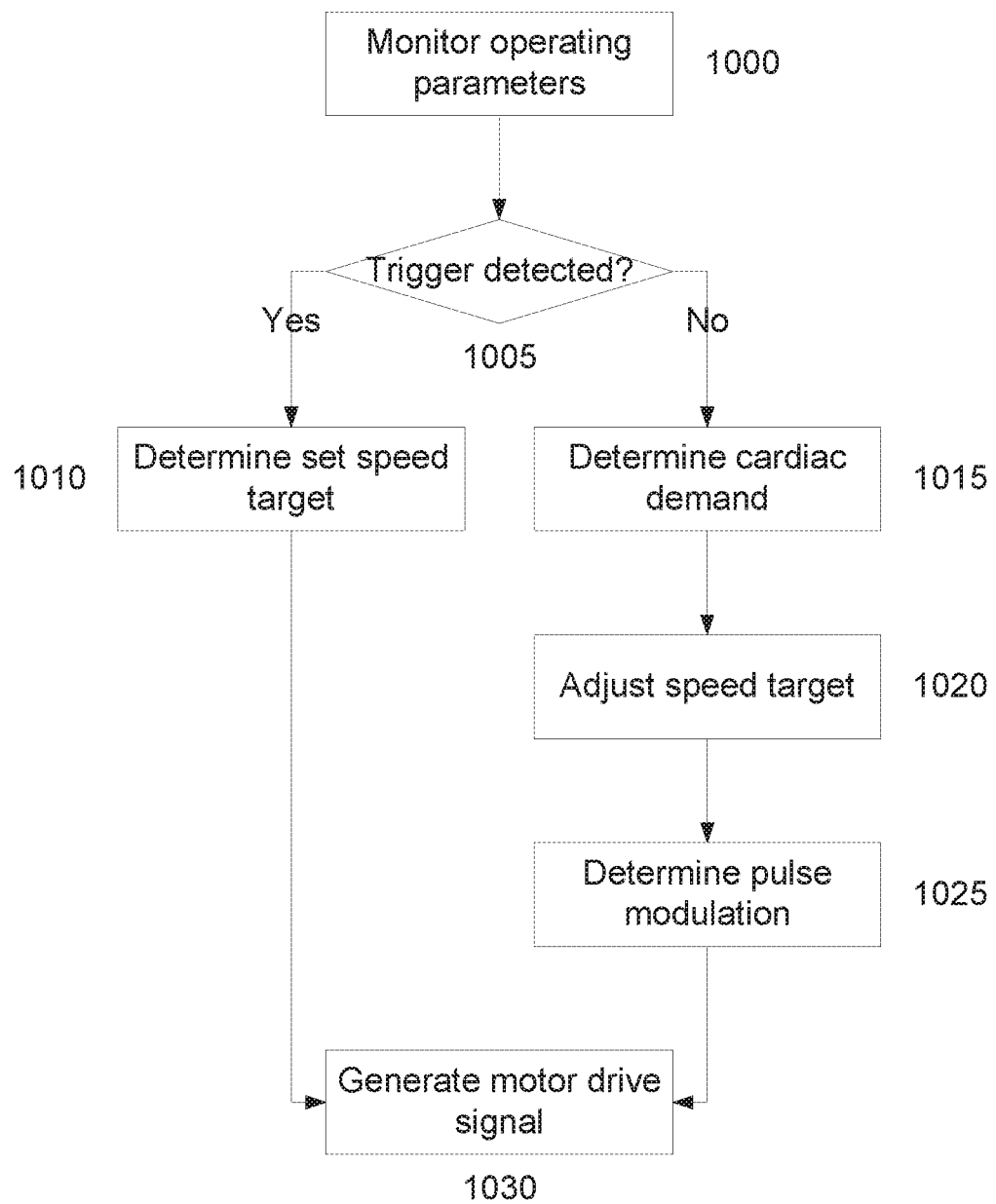
FIG. 10 is a flow chart of an example of a process for controlling impeller rotational speed.

A specific example for a control algorithm will now be described with reference to FIG. 10.

In this example, the controller monitors operating parameters at step 1000, using the operating parameters to determine if a trigger event has occurred, as will be described in more detail below. If so, the controller determines a set target speed at step 1010, using the set speed to generate a control signal that can be applied to the drive at step 1030.

After a predetermined amount of time, the controller typically increases the impeller speed to the original speed, and returns to step 1000, allowing the process to be repeated.

The set target speed is stored in a memory and retrieved as required, and can be a default speed, a speed set by a speed control algorithm and/or a speed set by an operator. The target speed may be defined as an absolute speed, such as 1800 RPM, or can be a relative speed, such as 300 RPM less than the current speed. Additionally, the set target speed might vary depending on a particular trigger which has been detected. For example, a bearing control desynchronization might have a different set target to a low pressure suction event.

Additionally, the set target might vary if multiple triggers are detected in a defined time period. For example, if a suction event occurs, the impeller speed might initially be reduced by 200 RPM, for a time period such as a few seconds, before the speed is returned to the original speed at which the pump was operating at prior to the triggered event. If a further suction event occurs within a given time period, such as the next five minutes, the speed can be reduced by 300 RPM, for a period of time, such as a few seconds, before the speed in increased to a value that is 100 RPM less than the original speed that the pump was operating at prior to the triggered event. However it will also be appreciated that in general a minimum defined speed is set, at which point further suction events will not decrease the speed further. For example four suction events in one minute might reduce the speed down to the lowest possible speed, say 1500 rpm. If another suction event occurs the speed will not be further decreased. Such a minimum speed would typically defined to ensure the patient has sufficient cardiac output. In this situation, if the speed has reached a minimum, and further suction events occur, an alert or notification might be provided to an overseeing operator.

If no trigger has been detected at step 1005, the controller typically operates to determine a cardiac demand at step 1015. In one example, this is performed based on a bearing current, in particular using the techniques previously described with respect to FIGS. 5A and 5B. In this example, the controller monitors changes in the bearing indicator in response to a perturbation, with the changes being at least partially indicative of cardiac demand.

At step 1020, the demand is used to adjust a speed target, which may optionally take into account a default speed or speed range, and/or a speed or speed range set by an operator. Thus, the controller controls the drive to thereby selectively change a rotational speed of the impeller at least partially in accordance with changes in the bearing indicator. At step 1025, pulse modulations are determined, for example to generate a physiological pulse, perturbation pulse (to assist in detection of cardiac demand) and/or washout pulse, before this is used to generate a motor drive signal at step 1030.

As previously mentioned, in one example, when the heart pump includes a magnetic bearing including at least one bearing coil that controls an axial position of the impeller within the cavity, the operating parameters include a bearing indicator at least partially indicative of operation of the magnetic bearing. However, this is not essential and other indicators can be used, such as a position of the impeller within the cavity as determined by a position sensor, a drive indicator indicative of operation of a drive or impeller rotational speed or the like.

Figure 11:
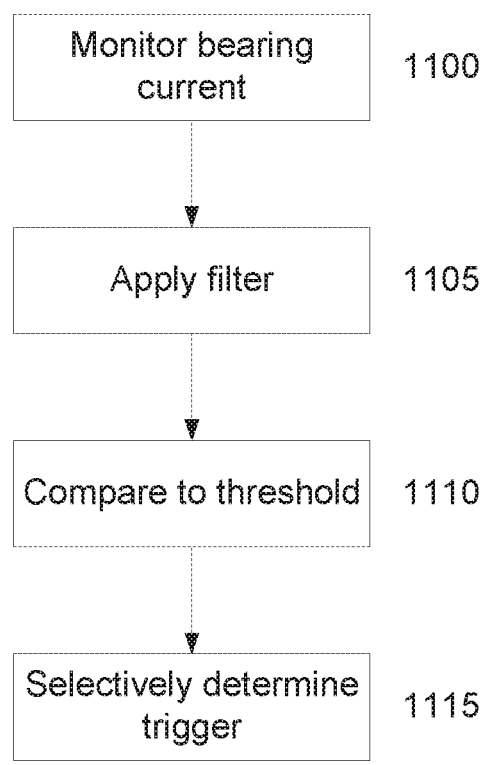
FIG. 11 is a flow chart of an example of a process for identifying a trigger event.

An example of the process for using the magnetic bearing indicator to determine a trigger event is shown in FIG. 11.

In this example, at step 1100, the bearing current is monitored, with a filter being applied at step 1105. The filter can be a low pass, or band pass filter, depending on the particular aspects of pump operation being monitored. At step 1110, the filtered bearing indicator is compared to a threshold, with results of the comparison being used to determine if a trigger has occurred at step 1115.

As an alternative to comparing the filtered bearing indicator to a threshold, alternatively, the system can determine a difference between an expected bearing indicator and a measured bearing indicator compare the difference to a threshold, which can be used to assess if the pump is operating as expected.

In one example, the system detects low frequency issues using a low pass filter having a cut-off of 0.2 Hz, detecting a trigger if the filter exceeds a ±1.2 A variation. The system detects high frequency issues using a low pass filter having a cut-off of 25 Hz, detecting a trigger if the filter exceeds a ±1.6 A variation. Finally, the controller detects excessive bearing forces using a low pass filter having a cut-off of 1 Hz, and when the difference between the bearing current and expected bearing current exceeds ±0.25 A.

Figure 12:
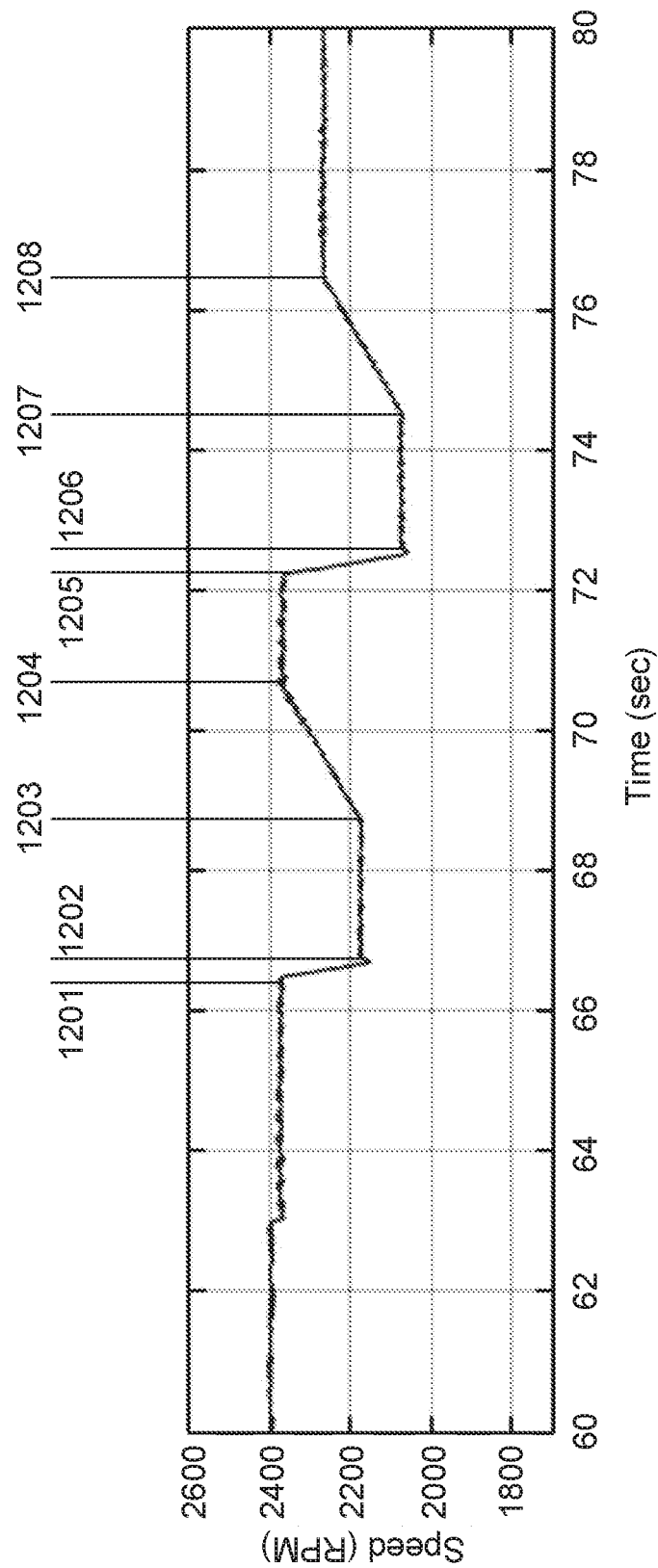
FIG. 12 is a graph showing an example of the control process of FIG. 10 responding to triggers.

An example of a resulting impeller rotational speed profile is shown in FIG. 12.

In this example, normal variations in impeller rotational speed are implemented until a trigger event, and in particular a suction event occurs at 1201, at which point the speed is dropped by 200 RPM for two seconds at 1202. At 1203 the speed is progressively increased to the original value at 1204. At 1205 a second suction event occurs, with the speed being dropped by 300 RPM for two seconds at 1206. Following this at 1207, the speed is increased to the original speed less 100 RPM at 1208. The impeller rotation speed is then maintained for five minutes before returning to the original speed.

An example of the process for matching cardiac demand will now be described with reference to FIGS. 13A to 13G.

Figure 13A:
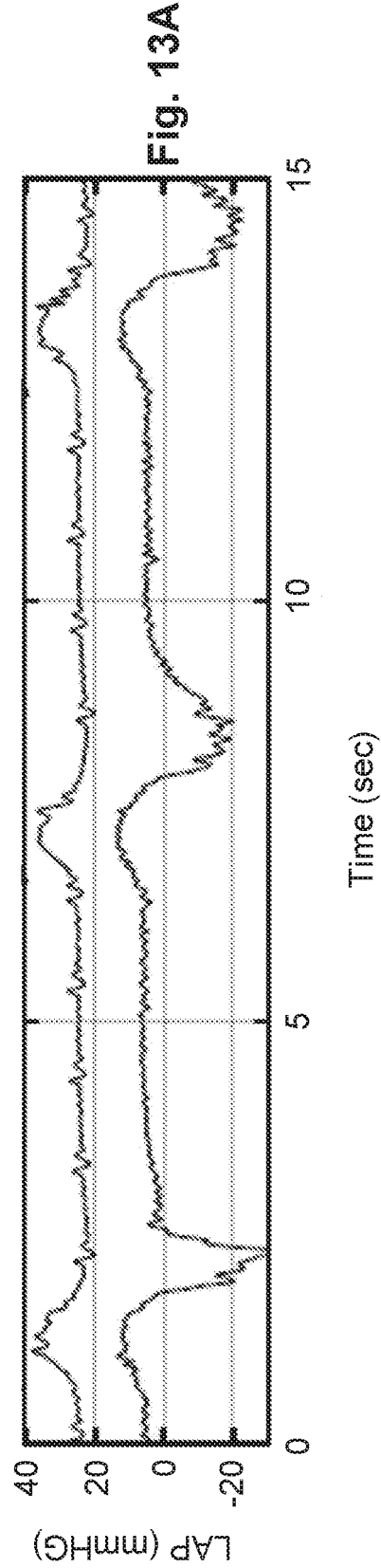
FIG. 13A is a graph of an example of changes in left arterial pressure in response to respiration during activity and when resting.
Figure 13B:
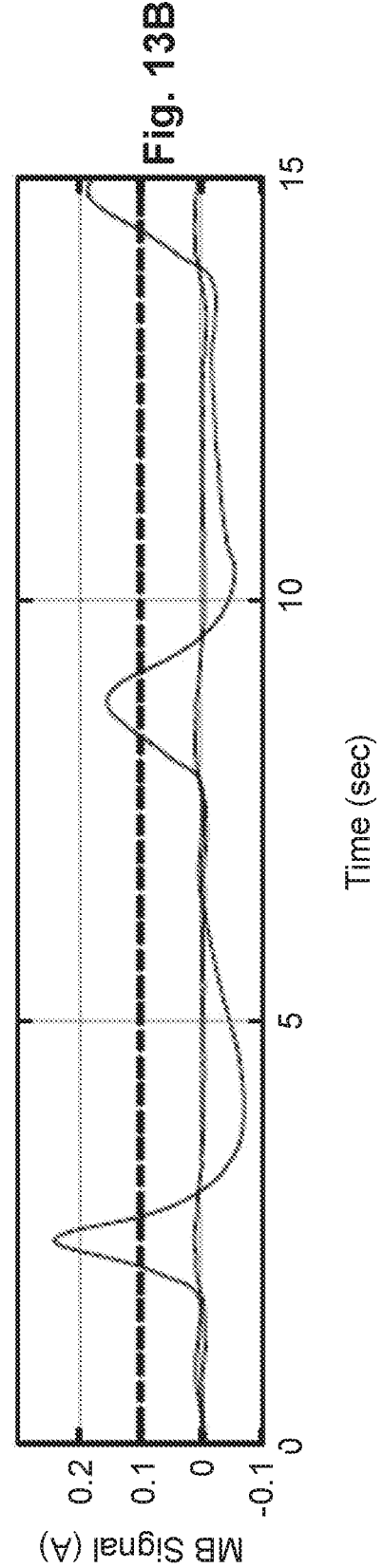
FIG. 13B is a graph of an example of changes in magnetic bearing current for the left arterial pressure of FIG. 13A.

FIGS. 13A and 13B show changes in left atrial pressure (LAP) and corresponding changes in bearing current respectively. For the upper line in FIG. 13A, this is at rest, with peaks corresponding to breathing events that lead to an increase LAP. The lower line corresponds to a situation in which the patient is exercising, which changes the level of atrial filling, leading to low atrial volumes, which in turn lead to a drop in atrial pressure following breathing. As shown this leads to a noticeable impact on magnetic bearing current, allowing low pressure scenarios to be detected.

Figure 13C:
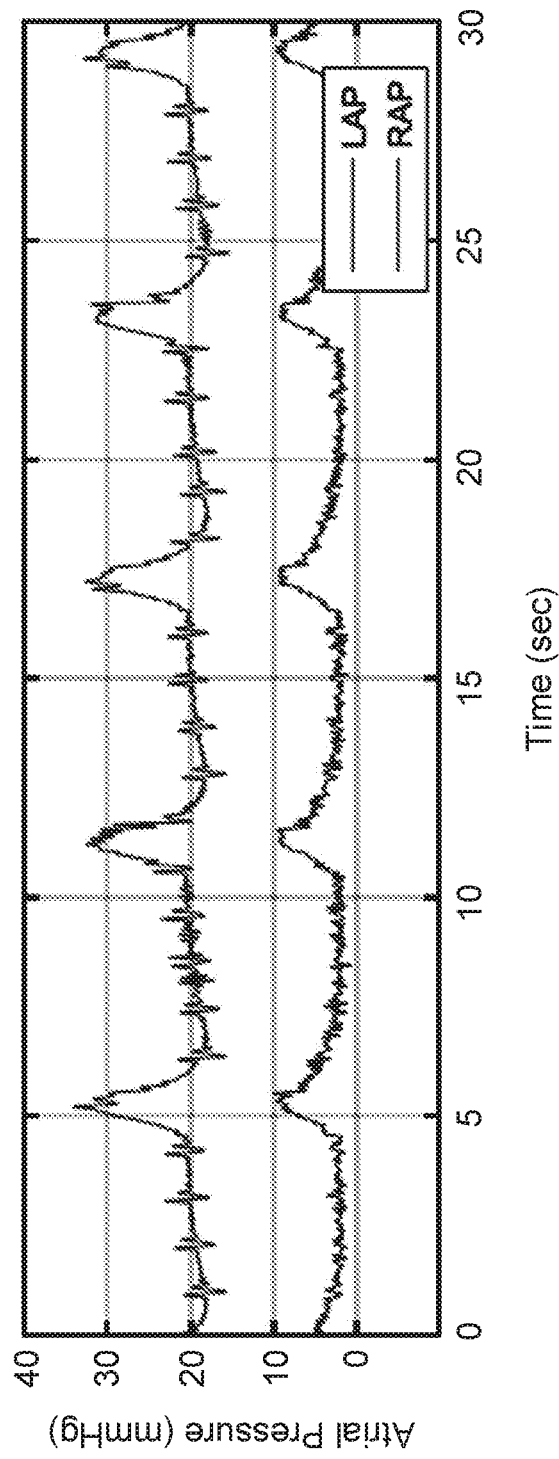
FIG. 13C is a graph of an example of changes in left and right arterial pressure in response to respiration.
Figure 13D:
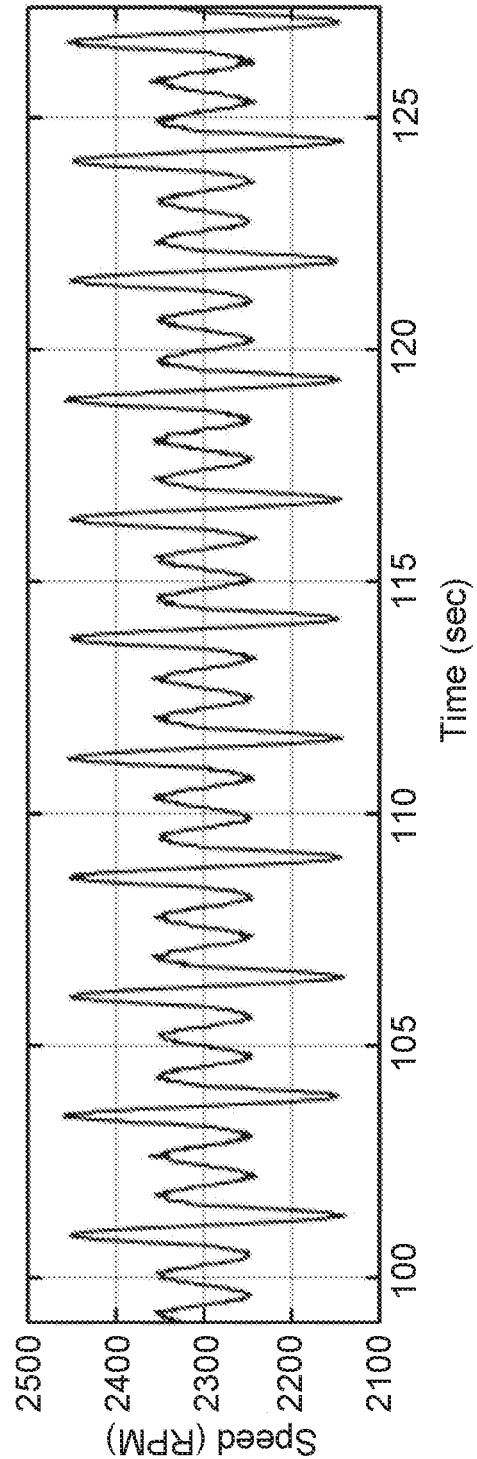
FIG. 13D is a graph of an example of changes in impeller rotational speed to induce changes in magnetic bearing current.

As previously described perturbations can therefore be used to detect the onset of such low pressure events, and examples of the perturbations can including respiration, which as shown in FIG. 13C leads to changes in left and right atrial pressure. Alternatively, this can be achieved using a search pulse, as shown in FIG. 13D, with the search pulse including a larger magnitude pulse between other pulses, such as physiological pulses or small washout pulses.

Figure 5A:
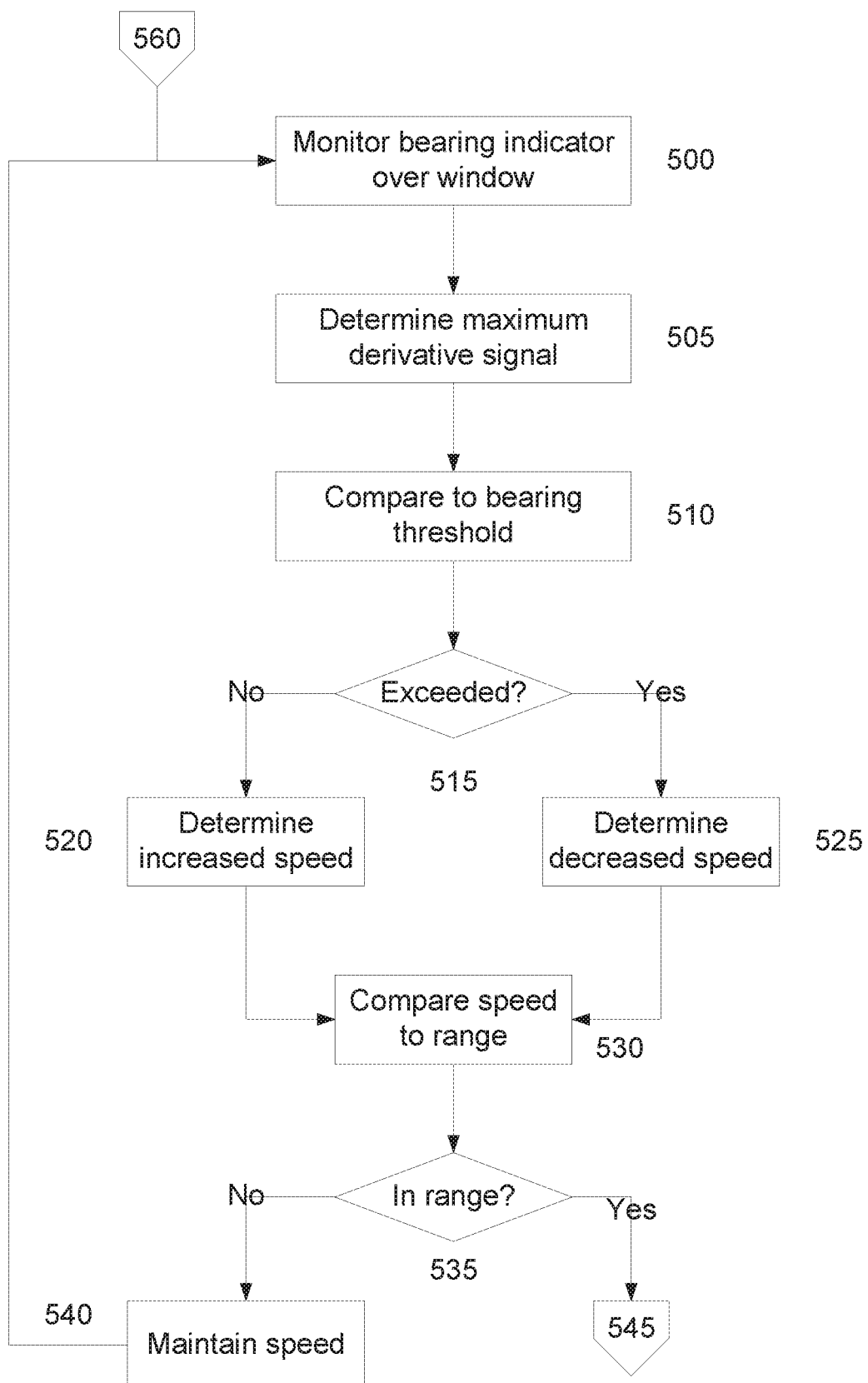
FIGS. 5A and 5B are a flow chart of a specific example of a speed controller process.
Figure 5B:
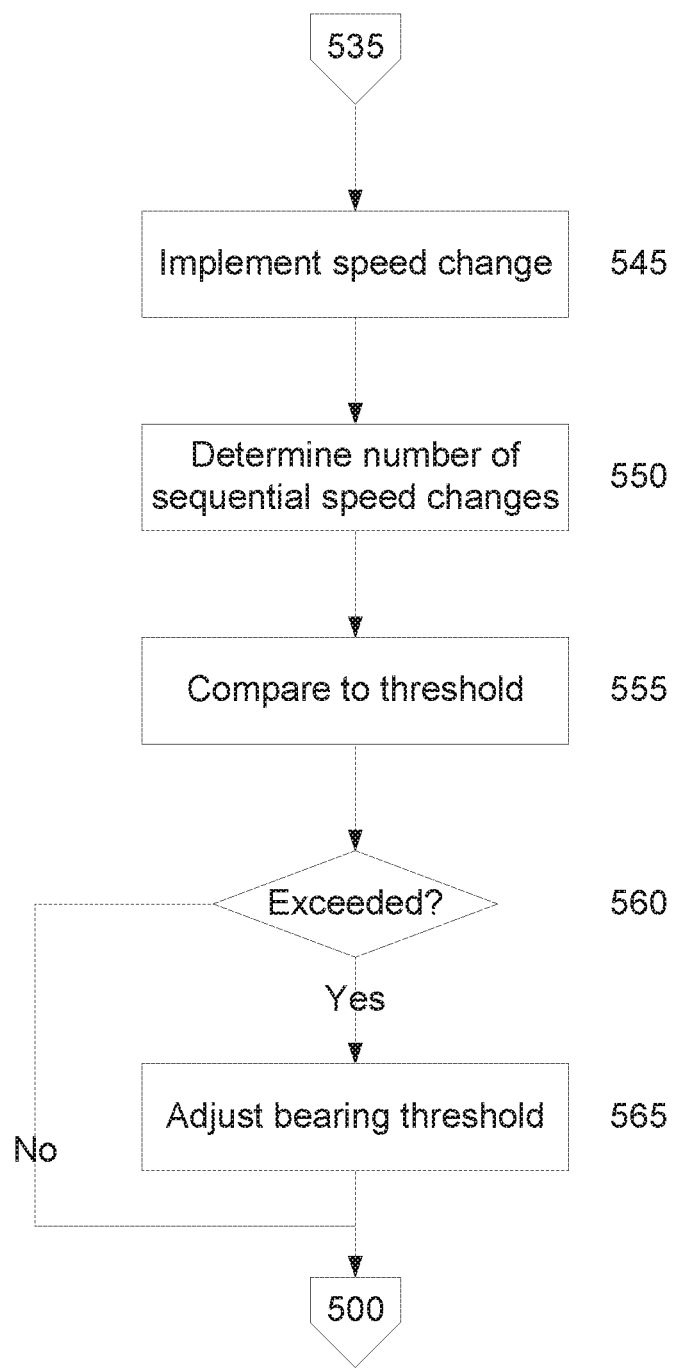

In the event that low pressure events are detected, the impeller flow is reduced, whereas otherwise the flow is increased, as previously described with respect to FIGS. 5A and 5B. The changes can be achieved using stepwise changes in base rotational speed as shown in FIG. 13E, or by increasing/decreasing pulse magnitude or pulse frequency as shown in FIGS. 13F and 13G, respectively.

A first specific example will now be described with reference to FIGS. 14A to 14C.

Figure 14A:
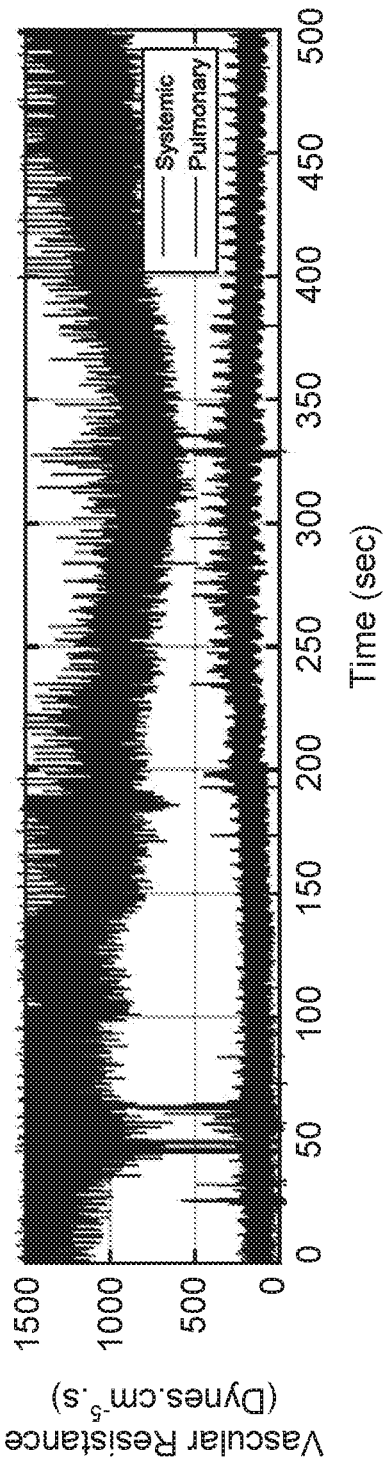
FIG. 14A is a graph of a first example of changes in systemic and pulmonary vascular resistances.
Figure 14B:
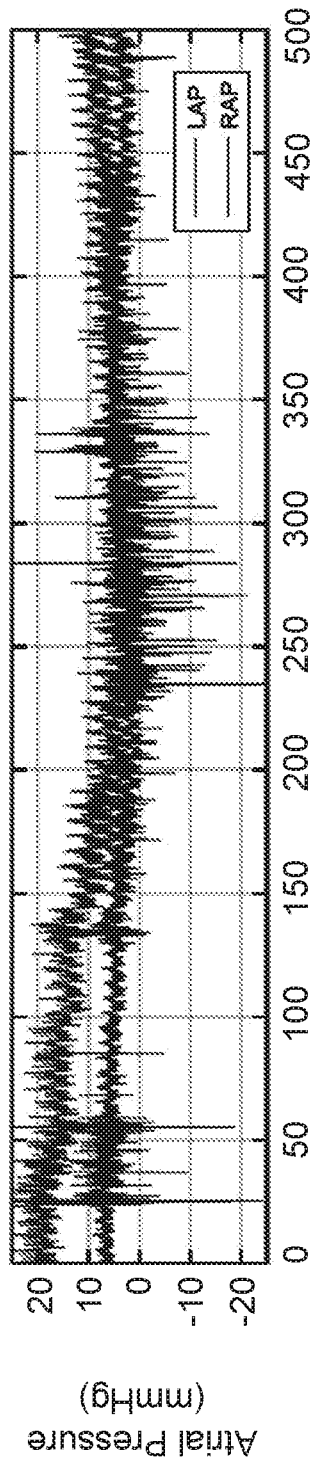
FIG. 14B is a graph of an example of changes in left and right arterial pressure for the systemic and pulmonary vascular resistances of FIG. 14A.
Figure 14C:
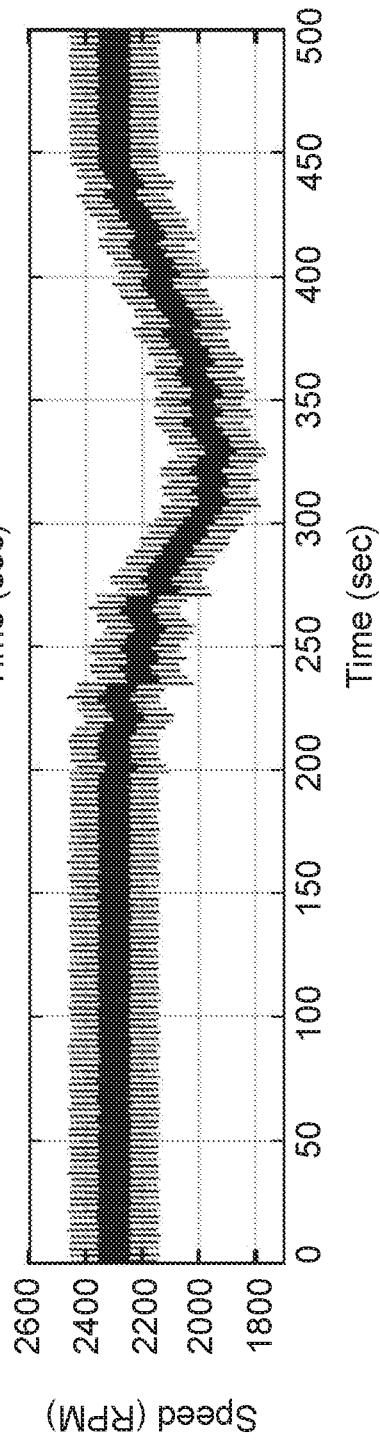
FIG. 14C is a graph of an example of changes in impeller rotational speed for the systemic and pulmonary vascular resistances of FIG. 14A.

In this example, the systemic and pulmonary resistance is shown in FIG. 14A, with corresponding atrial pressures and impeller pump speed being shown in FIGS. 14B and 14C respectively. In this example, a drop in systemic vascular resistance leads to a drop in left atrial pressure, with the pump speed initially remaining high. At time 200 secs, the higher amplitude search pulse leads to a spike in LAP, which triggers a speed reduction. As SVR continues to drop, further spikes in LAP occur, with the pump speed being reduced until time 325, at which point SVR starts to rise and size and frequency of LAP spikes reduce. Following this, the pump speed is increased until it returns to a baseline value at time 450.

Figure 14D:
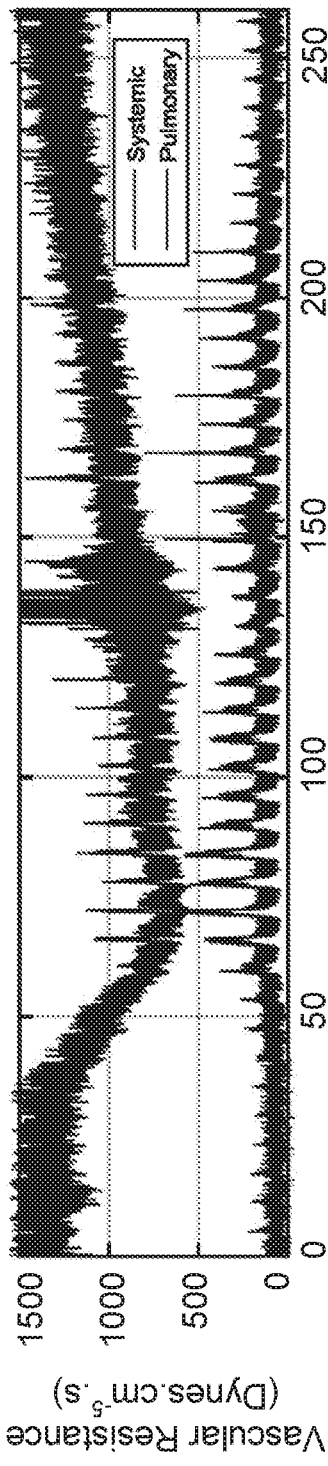
FIG. 14D is a graph of a second example of changes in systemic and pulmonary vascular resistances.
Figure 14E:
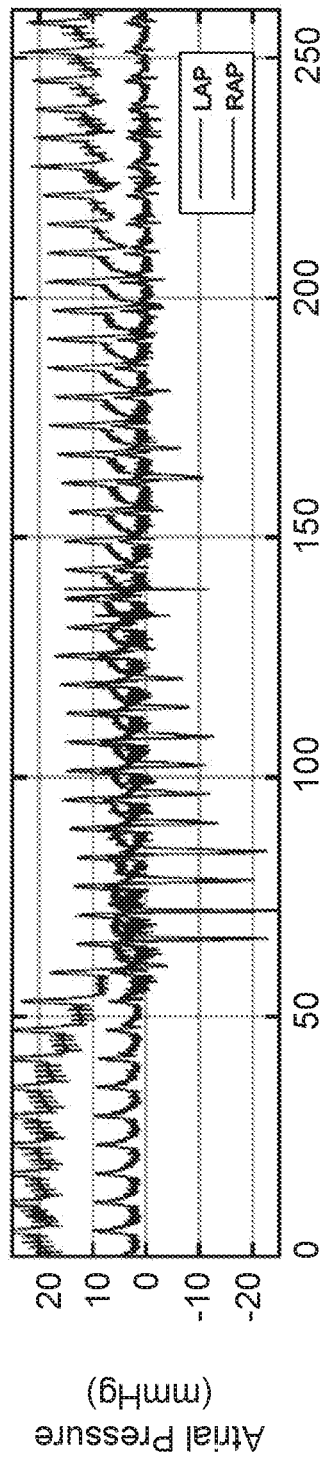
FIG. 14E is a graph of an example of changes in left and right arterial pressure for the systemic and pulmonary vascular resistances of FIG. 14D; and, FIG. 14F is a graph of an example of changes in impeller rotational speed for the systemic and pulmonary vascular resistances of FIG. 14D.
Figure 14F:
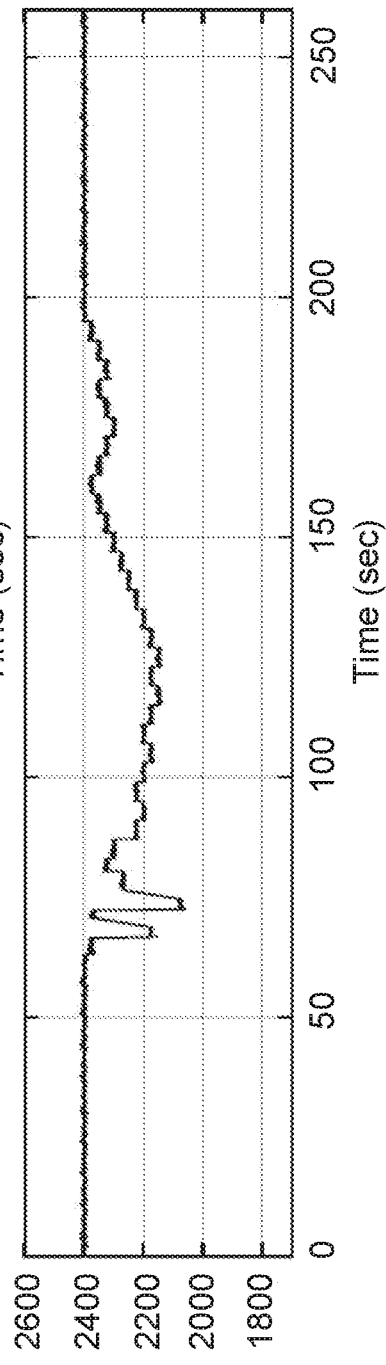

A second specific example is shown in FIGS. 14D to 14F, in which similar events occur, with the SVR dropping, leading to spikes in LAP, which in turn causes impeller speed to be reduced. As SVR returns to normal, the speed is increased.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers. As used herein and unless otherwise stated, the term "approximately" means±20%.

Persons skilled in the art will appreciate that numerous variations and modifications will become apparent. All such variations and modifications which become apparent to persons skilled in the art, should be considered to fall within the spirit and scope that the invention broadly appearing before described, including equivalents.

What is claimed is:

1. A heart pump including:
   a) a housing forming a cavity including at least one inlet and at least one outlet;

b) an impeller provided within the cavity, the impeller including vanes for urging fluid from the inlet to the outlet upon rotation of the impeller;
c) a drive that rotates the impeller within the cavity;
d) a magnetic bearing including at least one bearing coil that controls an axial position of the impeller within the cavity; and,
e) a controller including an electronic processing device that:
  i) monitors changes in a bearing indicator in response to a perturbation in blood flow, the bearing indicator being at least partially indicative of operation of the magnetic bearing; and,
  ii) controls the drive to thereby selectively change a rotational speed of the impeller at least partially in accordance with changes in the bearing indicator, wherein the controller controls the drive to selectively change the rotational speed of the impeller and thereby vary a blood flow rate through the heart pump to thereby induce at least one pulse and wherein the controller is adapted to vary overall flow rates through the pump to ensure adequate blood flow is achieved for a range of physiological states for a subject by altering at least one of:
    (1) a rotational speed profile, the rotational speed profile including changes in rotational speeds and having a major peak and a minor peak used to induce pulsatile flow similar to that induced by a human heart;
    (2) a duration of at least part of a pulse;
    (3) a pulse magnitude defined by a difference between an upper and lower rotational speed; and,
    (4) a pulse frequency,
    wherein the range of physiological states comprises the subject resting and the subject moving.

2. A heart pump according to claim 1, wherein the bearing indicator is indicative of at least one of:
a) a tilt of the impeller;
b) an electrical current used by the magnetic bearing;
c) an axial position of the impeller within the cavity;
d) a change in tilt of the impeller;
e) a rate of change in tilt of the impeller;
f) a change in electrical current used by the magnetic bearing;
g) a rate of change in electrical current used by the magnetic bearing;
h) a change in axial position of the impeller within the cavity; and,
i) a rate of change in axial position of the impeller within the cavity.

3. A heart pump according to claim 1, wherein the controller:
a) compares the change in bearing indicator to a bearing threshold; and,
b) controls the rotational speed in response to results of the comparison by:
  i) selectively decreasing the rotational speed of the impeller in response to the change in bearing indicator exceeding the bearing threshold; and,
  ii) selectively increasing the rotational speed of the impeller in response to the change in bearing indicator not exceeding the bearing threshold.

4. A heart pump according to claim 3, wherein the controller:
a) compares the bearing indicator change to multiple bearing thresholds; and,
b) controls the rotational speed in response to results of the comparison.

5. A heart pump according to claim 3, wherein the bearing threshold is adjusted based on at least one of:
a) a number of successive rotational speed changes;
b) a drive indicator at least partially indicative of operation of the drive;
c) changes in rotational speed of the impeller; and,
d) an impeller position.

6. A heart pump according to claim 3, wherein the controller:
a) monitors the bearing indicator over a set time period;
b) determines a maximum change in bearing indicator during the set time period; and,
c) compares the maximum change to the bearing threshold.

7. A heart pump according to claim 3, wherein the change in bearing indicator is at least partially indicative of at least one of:
a) a set blood pressure;
b) a suction event;
c) connection conduit collapse;
d) connection conduit deformation;
e) vasculature collapse; and,
f) vasculature deformation.

8. A heart pump according to claim 3, wherein the controller is adapted to change the bearing threshold dynamically as the drive is controlled.

9. A heart pump according to claim 3, wherein the controller is adapted to:
a) determine a number of successive rotational speed changes;
b) compare the number to a respective threshold; and
c) adjust the bearing threshold in response to the results of the comparison.

10. A heart pump according to claim 3, wherein the controller is adapted to select the bearing threshold based on a drive indicator at least partially indicative of operation of the drive.

11. A heart pump according to claim 1, wherein the controller:
a) determines a drive indicator at least partially indicative of at least one of:
  i) operation of the drive;
  ii) a current supplied to the drive;
  iii) an expected rotational speed of the impeller;
  iv) an actual rotational speed of the impeller; and,
  v) a magnitude of a rotational speed change;
b) determines a combined indicator based on a combination of the bearing indicator and the drive indicator; and,
c) controls the drive to thereby selectively change a rotational speed of the impeller at least partially in accordance with the combined indicator.

12. A heart pump according to claim 1, wherein the perturbation is at least one of:
a) a physiological perturbation;
b) a pump operation perturbation;
c) a heart beat of the subject;
d) aspiration of the subject;
e) a change in pump rotational speed; and,
f) a change in axial position of the impeller.

13. A heart pump according to claim 12, wherein the controller monitors changes in the bearing indicator at least partially in accordance with a frequency of the perturbations.

14. A heart pump according to claim 1, wherein the controller controls the rotational speed of the impeller so as to maximize the rotational speed of the impeller whilst avoiding a low pressure condition by:
a) using the change in bearing indicator to determine an onset of a low pressure condition including at least one of:
i) a suction event;
ii) connection conduit collapse;
iii) connection conduit deformation;
iv) vasculature collapse; and,
v) vasculature deformation; and,
b) selectively decreasing the rotational speed of the impeller in response to the onset being detected.

15. A heart pump according to claim 1, wherein:
a) the impeller includes first and second sets of vanes provided on a rotor body, the rotor being positioned within the cavity to define:
i) a first cavity portion having a first inlet and a first outlet, the first set of vanes being provided within the first cavity portion so as to define a first pump that provides at least partial left ventricular function; and,
ii) a second cavity portion having a second inlet and a second outlet, the second set of vanes being provided within the second cavity portion so as to define a second pump that provides at least partial right ventricular function and wherein at least one of:
(1) the axial position of the impeller determines a separation between each set of vanes and a respective cavity surface, the separation being used to control the fluid flows from the inlets to the outlets; and,
(2) the first and second pumps have respective pump performance curves having different gradients so that a change in rotational speed of the pump causes a change in the relative flows of the first and second pumps;
b) the drive is positioned at a first end of the cavity and includes:
i) a number of circumferentially spaced permanent magnets mounted in the rotor of the impeller, adjacent magnets having opposing polarities; and,
ii) at least one drive coil that in use generates a magnetic field that cooperates with the magnetic material allowing the impeller to be rotated;
c) the magnetic bearing is positioned at a second end of the cavity and includes:
i) first and second annular magnetic bearing members mounted within and proximate a face of the rotor, the first magnetic bearing member being provided radially outwardly of the second magnetic bearing member;
ii) a number of circumferentially spaced substantially U-shaped bearing stators mounted in the housing proximate a second end of the cavity, each U-shaped bearing stator having first and second bearing stator legs substantially radially aligned with the first and second magnetic bearing members respectively; and,
iii) at least one bearing coil on each bearing stator that generates a magnetic field that cooperates with the magnetic bearing members to thereby at least one of:
(1) control an axial position of the impeller; and,
(2) at least partially restrain radial movement of the impeller; and,
d) the heart pump is at least one of:
i) a ventricular assist device; and,
ii) a total artificial heart.

16. A heart pump according to claim 1, wherein the change in rotational speed is performed so as to at least one of:
a) induce the pulsatile flow, the pulsatile flow including a series of pulses and wherein for each pulse the controller:
i) creates a spike in the rotational speed;
ii) creates a major peak in the rotational speed, the major peak having a magnitude smaller than the spike; and,
iii) creates a minor peak in the rotational speed, the minor peak having a magnitude smaller than the major peak; and,
b) periodically reduce the rotational speed from a baseline speed at least one of:
i) to below a threshold value to create a washout pulse; and,
ii) to induce a physiological pulse.

17. A heart pump according to claim 1, wherein the controller:
a) monitors operating parameters of the heart pump to detect a trigger; and,
b) at least one of:
i) in response to detection of a trigger at least one of:
(1) controls the drive to rotate the impeller at a set rotational speed; and,
(2) generates an alert indicative of the trigger; and,
ii) in response to no detection of a trigger, controls the drive to rotate the impeller at a target rotational speed determined at least partially in accordance with a cardiac demand.

18. A controller for a heart pump, the controller including an electronic processing device that:
a) monitors changes in a bearing indicator in response to a perturbation in blood flow, the bearing indicator being at least partially indicative of operation of a magnetic bearing including at least one bearing coil that controls an axial position of an impeller within a cavity; and,
b) controls a drive that rotates the impeller within the cavity to thereby selectively change a rotational speed of the impeller at least partially in accordance with changes in the bearing indicator, wherein the controller controls the drive to selectively change the rotational speed of the impeller and thereby vary a blood flow rate through the heart pump to thereby induce at least one pulse and wherein the controller is adapted to vary overall flow rates through the pump to ensure adequate blood flow is achieved for a range of physiological states for a subject by altering at least one of:
(1) a rotational speed profile, the rotational speed profile including changes in rotational speeds and having a major peak and a minor peak used to induce pulsatile flow similar to that induced by a human heart;
(2) a duration of at least part of a pulse;
(3) a pulse magnitude defined by a difference between an upper and lower rotational speed; and,
(4) a pulse frequency,
wherein the range of physiological states comprises the subject resting and the subject moving.

19. A method of controlling a heart pump, the method including:
a) monitoring changes in a bearing indicator in response to a perturbation in blood flow, the bearing indicator being at least partially indicative of operation of a magnetic bearing including at least one bearing coil that controls an axial position of an impeller within a cavity; and, b) controlling a drive that rotates the impeller within the cavity to thereby selectively change a rotational speed of the impeller at least partially in accordance with the bearing indicator change, wherein the drive is controlled to selectively change the rotational speed of the impeller and thereby vary a blood flow rate through the heart pump to thereby induce at least one pulse and wherein overall flow rates through the pump are varied to ensure adequate blood flow is achieved for a range of physiological states for a subject by altering at least one of:

(1) a rotational speed profile, the rotational speed profile including changes in rotational speeds and having a major peak and a minor peak used to induce pulsatile flow similar to that induced by a human heart;

(2) a duration of at least part of a pulse;

(3) a pulse magnitude defined by a difference between an upper and lower rotational speed; and, (4) a pulse frequency, wherein the range of physiological states comprises the subject resting and the subject moving.

* * * * *